(12) United States Patent
Santerre

(10) Patent No.: US 6,770,725 B2
(45) Date of Patent: Aug. 3, 2004

(54) BIOACTIVE SURFACE MODIFIERS FOR POLYMERS AND ARTICLES MADE THEREFROM

(76) Inventor: Paul J. Santerre, University of Toronto, Faculty of Dentistry, Department of Biomaterials 124 Edwards St., Toronto, Ontario (CA), M5G 1G8

(*) Notice: Subject to any disclaimer, the term of this patent is extended or adjusted under 35 U.S.C. 154(b) by 119 days.

(21) Appl. No.: 10/162,084

(22) Filed: Jun. 5, 2002

(65) Prior Publication Data

US 2003/0097120 A1 May 22, 2003

(30) Foreign Application Priority Data

Jun. 7, 2001 (CA) .............................................. 2349989

(51) Int. Cl.$^7$ ................................................. C08H 1/00
(52) U.S. Cl. ............................ 528/29; 528/38; 528/65; 528/66; 528/70; 528/335; 528/359; 528/401; 528/391; 528/392; 528/44; 530/300; 530/345
(58) Field of Search .............................. 528/70, 38, 29, 528/65, 66, 335, 359, 401, 44, 391, 390; 530/300, 345

(56) References Cited

U.S. PATENT DOCUMENTS

| | | | |
|---|---|---|---|
| 4,861,830 A | 8/1989 | Ward, Jr. ...................... | 525/92 |
| 5,235,003 A | 8/1993 | Ward et al. .................. | 525/476 |
| 5,405,919 A | 4/1995 | Keefer et al. ................ | 525/377 |
| 5,589,563 A | * 12/1996 | Ward et al. .................... | 528/44 |
| 5,798,115 A | 8/1998 | Santerre et al. ............. | 424/423 |
| 5,954,966 A | 9/1999 | Matsuura et al. ............ | 210/640 |
| 6,127,507 A | * 10/2000 | Santerre ....................... | 528/66 |
| 6,503,538 B1 | * 1/2003 | Chu et al. .................... | 424/497 |

FOREIGN PATENT DOCUMENTS

| | | | |
|---|---|---|---|
| EP | 0 231 927 A2 | | 8/1987 |
| EP | 533 809 | * | 7/1997 |
| WO | WO 97/06195 | | 2/1997 |

OTHER PUBLICATIONS

Santerre et al, Journal of Applied Polymer Science, vol. 52, 515–523 (1994).
Modak et al, Surgery, Gynecology & Obstetrics, 164:143–147 (1987).
Bach et al, Journal of Antimicrobial Chemotherapy, 37:315–322 (1996).
Nathan et al, Bioconjugate Chem., 4:54–62 (1993).
Roseeuw et al, Journal of Materials Science: Materials in Medicine, 10:743–746 (1999).
Phaneuf et al, Journal of Biomedical Materials Research, 27:233–237 (1993).
Woo et al, Biomaterials, 21:1235–1246 (2000).

* cited by examiner

*Primary Examiner*—Margaret G. Moore
(74) *Attorney, Agent, or Firm*—Morgan, Lewis & Bockius LLP

(57) ABSTRACT

This invention relates to macromolecule modifiers containing biologically active drugs/biomolecules, or precursors thereof, and fluoroligomers; compositions comprising the macromolecules containing the drugs and fluoroligomers in admixture with polymers, particularly biomedical polymers; articles made from the admixtures, particularly medical devices. Specifically, the modifier has the general formula $$[\text{fluoro}]-[\text{link B}]-[[\text{oligo}]-([\text{link A}]-[\text{oligo}])_n-[\text{link B}])]_m-[\text{fluoro}]$$
$$\quad\quad\quad\quad\quad\quad\quad | \quad\quad\quad\quad\quad\quad\quad\quad\quad\quad\quad\quad\quad | $$
$$\quad\quad\quad\quad\quad\quad [\text{Bio}] \quad\quad\quad\quad\quad\quad\quad\quad\quad\quad [\text{Bio}]$$

wherein $$[[\text{oligo}]-([\text{link A}]-[\text{oligo}])_n-[\text{link B}])]_m$$
$$\quad\quad\quad\quad\quad\quad\quad\quad\quad | $$
$$\quad\quad\quad\quad\quad\quad\quad [\text{Bio}]$$

is a central portion comprising an oligomeric polymeric segment having a theoretical molecular weight of less than 15,000, and being compatible with said base polymer; wherein

[oligo] is a first oligomeric segment;

[link A] is a second coupling segment linking one [oligo] to another [oligo] within said central portion;

n is 0 to 20;

[fluoro] is a polyfluoro oligomeric group; and

[link B] is a first coupling segment linking said central portion to said [fluoro] through said first coupling segment; and coupled to a bioactive moiety [Bio] or precursor thereof; and m is 1 to 20.

22 Claims, 3 Drawing Sheets

BIOACTIVE SURFACE MODIFIERS FOR POLYMERS AND ARTICLES MADE THEREFROM

FIELD OF THE INVENTION

This invention relates to macromolecules containing biologically active drugs/biomolecules, or precursors thereof, and fluoroligomers; compositions comprising said macromolecules containing biologically active drugs/biomolecules and fluoroligomers in admixture with polymers, particularly biomedical polymers; articles made from said admixtures, particularly medical devices; and methods of preparation of said macromolecules containing biologically active drugs/biomolecules and fluoroligomers.

BACKGROUND TO THE INVENTION

Biomedical polymers (includings polyamides, polyurethanes, polysilicones, polyfluorocarbons, polysulfones, polyolefins, polyesters, polyvinyl derivatives, polypeptide derivatives, polysaccharide derivatives etc.) are applied extensively in the manufacture of conventional biomedical devices used in contact with living tissues, body fluids and its constituents, such as vascular and skin grafts, endotracheal tubes and catheters, drug delivery vehicles and affinity chromatography systems [1]. Many synthetic polymers have characteristics that make them useful as biomedical materials. One reason for this is the wide range of properties available from man-made polymers. The chemistry of the repeat unit, the shape of the molecular backbone, and the existence and concentration of intermolecular bonds among the macromolecules that make up the polymeric material all influence its ultimate properties. Additional variations in polymer character is possible in polymers with more than one kind of repeating unit. Copolymers, terpolymers, and even multipolymers are possible in which the properties of more than one polymer type are combined to produce a unique material. The arrangement of the different repeat units in copolymers allows further property variations. The overall concentration of each monomer is also an important parameter in determining the properties of the copolymers, but unless one monomer is used in great excess over the other, the resulting properties can be quite different from either homopolymer.

Biocompatibility

Biocompatibility is defined as the ability of a material to perform with an appropriate host response in a specific application. The host relates to the environment in which the biomaterial is placed and will vary from being blood, bone, cartilage, heart, brain, etc. Despite the unique biomedical related benefits that any particular group of polymers may possess, the materials themselves, once incorporated into the biomedical device, may be inherently limited in their performance because of their inability to satisfy all the critical biocompatibility issues associated with the specific application intended. For instance while one material may have certain anti-coagulant features related to platelets it may not address key features of the coagulation cascade, nor be able to resist the colonization of bacteria. Another material may exhibit anti-microbial function but may not be biostable for longterm applications. The incorporation of multi-functional character in a biomedical device is often a biomedical device is often a complicated and costly process which almost always compromises one polymer property or biological function over another, yet all blood and tissue contacting devices can benefit from improved biocompatibility character. Clotting, toxicity, inflammation, infection, immune response in even the simplest devices can result in death or irreversible damage to the patient. Since most blood and tissue material interactions occur at the interface between the biological environment and the medical device, only the make-up of the outer molecular layer (at most the submicron layer) of the polymeric material is relevant to the biological interactions at the interface. This means that as long as the polymer does not contain any leachable impurities, the chemistry of the bulk polymer, which is distant from the biological interface, should have a minimal influence on tissue and body fluid interactions if the material surface is relatively biostable.

Surface Modification

Given the knowledge that it is the surface that is the most pertinent issue in the matters of biocompatibility, a practical approach taken towards the development of biomedical devices has involved the utilization of polymeric materials that satisfy the bulk material criteria for the device while applying some form of surface modification which may specifically tailor the biological surface properties and produce minimal change to the bulk character. Such an approach is seen advantages over grafting biologically active agents to the bulk polymer chains since the latter approach brings about significant changes to the physical structure of the polymers [2]. Methods that have been used for the surface modification of polymer surfaces rather than bulk grafting of the polymers have included the following: Non-covalent coatings (with and without solvent), chemical surface grafting, ion implantation, Langmuir-Blodgett Overlayer and self assembled films, surface modifying additives, surface chemical reactions and etching and roughning.

Surface Modifying Macromolecules

The use of oligomeric surface modifying additives present a significant advance over many commercial surface coating technologies reported above (i.e. radiation grafting polymerization; chemical coating, solvent coating; electron radiation; plasma polymerization or deposition; etc.), since it is a one step operation which can be simultaneously carried out with normal extrusion, film casting, fibre spinning and injection molding processes. The technology is readily transferable from one field to the next because it is adaptable to different polymer systems, analogous to additives such as colorants. General applications have included desoiling agents [3] and membrane applications for the separation of organics and water [4]. In areas of specific interest to the biomedical field, polymeric additives have been developed for applications in polyurethanes and other materials [5,6]. Ward et al. [7], issued describes polymer admixtures formed from a base polymer and thermoplastic copolymer additives having polar hard segments and polar and no-polar soft blocks in graft or block copolymer form, for use in biomedical devices. Ward et al. [7], describes novel linear polysiloxane-polylactone block copolymers, particular polysiloxane-polycaprolactone linear blocked copolymers, miscible with nylon for use as surface-modified nylon articles. Ward et al., [8] describes end-group containing polymers that comprise a linear base polymer having covalently bonded surface active end groups of a nature and present in an amount such that the polymer has a surface interaction tension that differs by at least 1 dyne/cm from the surface or interfacial tension of an otherwise identical polymer that does not contain the covalently bonded surface active endgroups. Santerre [6] describes fluoroligomers and compositions comprising fluoroligomers as surface-modifiers in admixture with polymers, for providing articles with passive surface properties, particularly, medical devices that shield enzyme interactions along with having acceptable passive blood compatibility.

It should be noted that in cases pertaining to the end group's described above [6,8], and the influence of the latter on cells, proteins and other biomolecular functions, the type of the interaction is relatively non-specific and it is preferred to be passive in nature, meaning that the surface generated by the end groups does not contain in itself a defined biochemical action that allows it to be both surface active and express a specific biological action on individual cellular mechanisms, specific protein or enzyme activity, or messenger action in the case of peptide signaling molecules. For the latter, the biomedical community still relies on traditional methods of therapy, i.e. the delivery of drugs or bio-active molecules via traditional diffusion mechanisms. Classically this has been achieved systemically but over the last decade a host of localized delivery vehicles have been developed and consist primarily of diffusion controlled systems or polymeric substrates with surface grafted drugs of bio-active molecules [9–11]. "For example, Santerre and Mittleman [9] teaches on the synthesis of polymeric materials using pharmacologically-active agents and monomers for polymers. The pharmacologically-active compounds provide in vivo enhanced long term anti-inflammatory, anti-bacterial, anti-microbial and/or anti-fungal activity."

Specifically, polymeric carriers have been developed, which contain drug moieties as terminal groups, or as pendent groups on the polymer chain. Polymers that are utilized for conjugation with drugs have included poly($\alpha$-amino acids), polysaccharides such as dextrans and chitin, polyurethanes and others. By copolymerizing amino acid moieties into the backbone of the polymer chains, Nathan [12] et al. have synthesized polyurethanes having pendent drugs to the amino acid unit. The specific conjugation of penicillin V and cephradine as pendant antibiotics to polyurethanes has been reported on by Nathan [12]. In the latter work the investigators showed that hydrolytically labile pendant drugs were cleaved and exhibited antimicrobial activities against S. aureus, E. faecalis and S. pyogenes. Others have described vinyl monomers with nalidixic acid, a quinolone antibiotic, coupled in a pendant manner to the active vinyl molecule, which was subsequently polymerized. In in-vivo hydrolysis studies they reported a 50% release of drug moities over the first 100 hours. This quinolone drug has been shown to be effective against gram negative bacteria in the treatment of urinary track infections, however chemical modifications of the latter (e.g. ciprofloxacin, norfloxacin and others) have a wider spectrum of activity. More recent work on the conjugation of norfloxacin to mannosylated dextran has been carried out in an effort to increase the drug's uptake by cells, enabling them to gain faster access to micro-organisms [13]. The studies showed that norfloxacin could be released from a drug/polymer conjugate by enzyme media and in in vivo studies, the drug/polymer conjugate was effective against Mycobacterium tuberculosis residing in liver [13]. In the later system, norfloxacin was attached pendent to sequences of amino-acids which permitted its cleavage by the lysosomal enzyme, cathepsin B.

In all drug conjugates, the goal has been to develop systems that would enhance either the drug activity and/or the diffusivity of the drug into an aqueous biological environment. In some instances the conjugates may be loaded into substrates, polymeric or non-polymeric, in order to have the conjugate gradually released from the substrate (i.e. controlled drug delivery). In other instances the drug may be actually grafted to the polymer matrix chains, either to remain permanently fixed or subsequently released via hydrolysis of the coupling bond. However, the latter limits the drug's diffusion among the polymer chains making up the matrix, thus limiting the delivery of the drug. It should be noted that in either case, i.e. the drug loading of a polymer matrix or coupling to a polymer matrix, there is the introduction of a significant effect on bulk polymer properties because the drug is distributed throughout the material. In the particular application of the latter systems, where drug delivery (i.e. biochemical function) is the key focus, and the physical function of the device rather than the biochemical function, may be secondary or have no function over the longterm (i.e. weeks to years), consideration to the changes in bulk structure are not a limitation of the device's primary function. However, such systems would not readily satisfy the physical demands of most implant devices (i.e. heart valves, vascular grafts, catheters, corneal lens, tendons, tissue scaffolds etc.) because they would compromise physical function which is important to the device's role. A drug conjugate applied to such system would however have a significant advantage if it could be surface specific rather than bulk distributed. Furthermore, if such a drug conjugate could achieve surface specificity without compromising the biochemical potential of the drug component, then one would have a means of generating simultaneous surface modification and introduction of specific biochemical function to the surface of an implant device (applied in body part replacement) or a structural scaffold (applied in tissue engineering or bio-reactor systems). This would provide the field with a truly unique technology which could rival existing systems since at the current time, there are few if any technologies related to biomaterials and their associated devices (i.e. vacular grafts, tendons, corneal lens, and the like), which simultaneously provide for a specific and stable surface modification of the biomaterial, by a drug or drug/conjugate loaded component.

Publications (1) Ratner B. D., Hoffman, A. S, Schoen F. J., Lemons, J. E., Biomaterials Science, "An Introduction to Materials in Medicine", Academic Press, San Diego, 1996.
(2) Santerre, J. P., Brash, J. L., J. Appl. Polym. Sci., 51, 515 (1994).
(3) Eur. Patent. Appl. 0,231,927, Submitted by Asahi Glass Company Ltd., Mar. 2, 1987.
(4) U.S. Pat. No. 5,954,966—Matsuura et al., issued Sep. 21, 1999.
(5) U.S. Pat. No. 4,861,830—Ward, Robert S., issued Aug. 29, 1989.
(6) U.S. Pat. No. 6,127,507—Santerre, Paul J. Oct. 3, 2000.
(7) U.S. Pat. No. 5,235,003—Ward, Robert S. Aug 10, 1993.
(8) U.S. Pat. No. 5,589,563—Ward, Robert R. and White, Kathleen A. Dec. 31, 1996.
(9) U.S. Pat. No. 5,798,115—Santerre, Paul J. and Mittleman, Marc W. Aug. 25, 1998.
(10) Modak S. M., Sampath, L., Fox, C. L., Benvenisty A., Nowygrod, R., Reemstmau, K. Surgery, Gynecology & Obstertrics ,164, 143–147 (1987).
(11) Bach, A.; Schmidt, H.; Böttiger, B.; Schreiber B.; B öhrer, H.; Motsch, J.; Martin, E.; Sonntag, H. G., J. Antimicrob. Chemother., 37, 315, (1996).
(12) Nathan, A.; Zalipsky, S.; Ertel, S. I.; Agarthos, S. N.; Yarmush, M. L.; Kohn. J. Bioconjugate Chem. 1993, 4, 54–62.
(13) Roseeuw, E.; Coessens V.; Schacht E., Vrooman B.; Domurado, D.; Marchal G. J Mater. Sci: Mater. Med 1999, 10, 743–746.

SUMMARY OF THE INVENTION

It is an object of the present invention to provide polymer compounds comprising biologically active molecules, such as, for example pharmaceuticals including anti-inflammatory, anti-oxidant, anti-coagulant, anti-microbial, cell receptor ligands and bio-adhesive molecules, oligonucleic acid sequences for DNA and gene sequence bonding, phospholipid head groups to provide cell membrane mimics or precursors thereof, and fluoroligomers.

It is a further object of the present invention to provide said polymer compounds in admixture with a compatible polymeric biomaterial or polymer composite biomaterial for providing a shaped article having improved surface properties.

It is a further object of the present invention to provide said shaped article for use as a medical device, comprising a body fluid and tissue contacting device in the biomedical sector, or in providing improved biocompatibility, or for use in the biotechnology sector for improving affinity column chromatography systems or promoting surface catalytic reactions.

It is a further object of the present invention to provide said polymer compounds in admixture with either a base polyurethane, polysilicone, polyester, polyethersulfone, polycarbonate, polyolefin or polyamide for use as said medical devices in the biomedical sector, or in providing improved biocompatibility, or for use in the biotechnology sector for improving affinity column chromatography systems, design diagnostics and biosensor chips or promoting surface catalytic reactions.

It is a further object of the invention to provide processes of manufacture of bioactive fluoroalkyl surface modifiers, said polymer compounds, said admixtures and said shaped articles.

The invention, generally, provides a bioactive fluoroalkyl surface modifier, herein termed a BFSM, having a central portion comprising oligomeric segments of <15,000 theoretical molecular weight and optional link segments, herein denoted [linka] covalently coupled to a first oligomeric segment denoted [oligo], such that the central portion is compatible with the polymeric material in which the BFSM is subsequently used in admixture, α-ω terminal polyfluoro oligomeric groups denoted [fluoro], non-optional coupled link segments herein denoted [linkB], wherein [linkB] is covalently coupled with the central portion and [fluoro] as well as being covalently or ionically coupled to a bioactive component.

Accordingly, the invention provides in one aspect, a bioactive fluoroalkyl surface modifier for use in admixture with a compatible base polymer, said modifier having the general formula

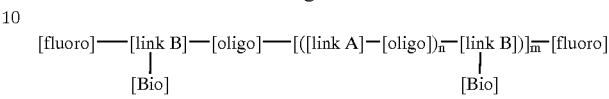

wherein

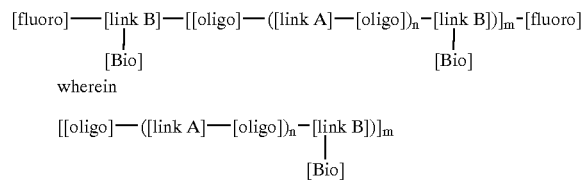

is a central portion comprising an oligomeric polymeric segment having a theoretical molecular weight of less than 15,000, and being compatible with said base polymer; wherein

[oligo] is a first oligomeric segment;

[link A] is a second coupling segment linking one [oligo] to another [oligo] within said central portion;

n is 0 to 20;

[fluoro] is a polyfluoro oligomeric group; and

[link B] is a first coupling segment linking said central portion to said [fluoro] through said first coupling segment; and coupled to a bioactive moiety [Bio] or precursor thereof; and m is 1 to 20.

In a preferred aspect the invention provides a modifier as hereinabove defined of the general formula

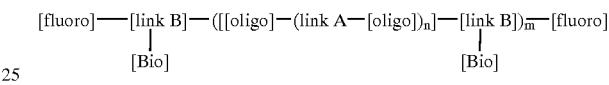

wherein n is 0–20; and m is 1–20; provided that when n is 0, m is 1.

In a further preferred aspect the invention provides a bioactive fluoroalkyl surface modifier for use in admixture with a compatible base polymer, said modifier having the general formula

[fluoro]—[link B]—([[oligo]—(link A—[oligo])$_n$]—[link B])$_{\overline{m}}$—[fluoro]
          |                                   |
          [Bio]                        [Bio]

wherein [[oligo]-(link A-[oligo])$_n$] is a central portion comprising an oligomeric polymeric segment having a theoretical molecular weight of less than 15,000, and being compatible with said base polymer;

[oligo] is a first oligomeric segment;

[link A] is a second coupling segment linking one [oligo] to another [oligo] within said central portion;

n is 0 to 20;

[fluoro] is a polyfluoro oligomeric group; and

[link B] is a first coupling segment linking said central portion to said [fluoro] through said first coupling segment; and coupled to a bioactive moiety [Bio] or precursor thereof; and m is 1 to 20.

Preferably, n is 2 to 10 and m is 1 to 10.

It can be seen in the above formula that [link B] is both within and outside of said central portion.

By the term "oligomeric segment" is meant a relatively short length of a repeating unit or units, generally less than about 20 monomeric units and molecular weights less than 5000. Preferably, [oligo] is selected from the group consisting of polyurethane, polyurea, polyamides, polyalkylene oxide, polycarbonate, polyester, polylactone, polysilicone, polyethersulfone, polyolefin, polyvinyl, polypeptide polysaccharide; and ether and amine linked segments thereof.

By the term "linkA molecule" is meant a molecule capable of covalently coupling oligo units together and to form said second coupling segments within said central portion. Typically, linkA molecules can have molecular weights ranging from 40 to 700 and have difunctionality to permit coupling of two oligo units. Preferably the linkA molecules selected from the group of diamines, diisocyanates, disulfonic acids, dicarboxylic acids, diacid chlorides and dialdehydes. Terminal hydroxyls, amines or carboxylic acids on the oligo molecules can react with diamines to form oligo-amides; react with diisocyanates to form oligo-urethanes, oligo-ureas, oligo-amides; react with disulfonic acids to form oligo-sulfonates, oligo-sulfonamides; react with dicarboxylic acids to form oligo-esters, oligo-amides; react with diacid chlorides to form oligo-esters, oligo-amides; and react with dialdehydes to form oligo-acetal, oligo-imines.

By the term "linkB molecule" is meant a molecule capable of providing primary functional groups capable of covalently coupling with the oligo/linkA central portion and fluoro group components, as well as simultaneously having secondary functional chemistry for coupling drug or bioactive components herein termed Bio to constitute said first coupling segment. Typically, linkB molecules have molecular weights ranging from 40 to 700. Preferably the linkB molecules are selected from the group of functionalized diamines, diisocyanates, disulfonic acids, dicarboxylic acids, diacid chlorides and dialdehydes, wherein the functionalized component has secondary functional chemistry that is accessed for chemical attachment of [Bio] components. Such secondary groups include, for example, esters, carboxylic acid salts, sulfonic acid salts, phosphonic acid salts, thiols, vinyls and secondary amines. Again, terminal hydroxyls, amines or carboxylic acids on the oligo/linkA intermediates can react with diamines to form oligo-amides; react with diisocyanates to form oligo-urethanes, oligo-ureas, oligo-amides; react with disulfonic acids to form oligo-sulfonates, oligo-sulfonamides; react with dicarboxylic acids to form oligo-esters, oligo-amides; react with diacid chlorides to form oligo-esters, oligo-amides; and react with dialdehydes to form oligo-acetal, oligo-imines.

Typically, the [fluoro] polyfluoro oligomeric group has a molecular weight ranging from 100 to 1500, and generally formed in the BFSM by reaction of the corresponding perfluoroalkyl group, having precursor monofunctional hydroxyl or amine groups, with the link B molecule.

Preferably, [fluoro] is selected from the group consisting of radicals of the general formula $CF_3(CF_2)_pCH_2CH_2-$ wherein p is 2–20 and $CF_3(CF_2)_m(CH_2CH_2O)_q$ wherein q is 1–10 and m is 1–20. More preferably [fluoro] is the perfluoroalkyl group $C_8F_{17}CH_2CH_2-$ By the term "drug or biologically active agent", or precursor thereof, is meant a molecule that can be coupled to linkB segment either via covalent or ionic bonding. The molecule must have some specific and intended pharmaceutical or biological action. Typically the [Bio] unit has a molecular weight ranging from 40 to 5000 but may be higher if it does not inhibit transport of the BFSM to the surface of the material being used to form the intended shaped articles. Preferably, the Bio unit is selected from the group of anti-inflammatory, anti-oxidant, anti-coagulant, anti-microbial, cell receptor ligands and bio-adhesive molecules, specifically oligo-peptides and oligo-saccharides, oligo-nucleic acid sequences for DNA and gene sequences bonding, and phospholipid head groups to provide cell membrane mimics. The Bio component must have at least one chemical function that can react with the secondary groups of the linkB component.

The oligomeric polymeric segment preferably has a molecular weight of <10,000; and more preferably, <5,000.

The term "theoretical molecular weight" in this specification is the term given to the absolute molecular weight that would result from the reaction of the reagents utililized to synthesize any given BFSM. A close confirmation of this absolute value can be ascertained by elemental analysis of the fluorine content which can be correlated to the final absolute molecular weight of the polymer. As is well known in the art, the actual measurement of the absolute molecular weight is complicated by physical limitations in the molecular weight analysis of polymers using gel permeation chromatography methods. Hence, in some instances, a polystyrene equivalent molecular weight is reported for gel permeation chromatography measurements. The latter number is merely of value in terms of reporting on reproducibility of the molecular weight for a given BFSM. It is the theoretical molecule weight (i.e. absolute molecular weight based on reagent stochiometry) which is of relevance in defining the limitations herein, since the latter defines the fluorine content. The fluorine content of the BFSM, preferably, should remain above 1 wt % in order to enable the molecule to effectively migrate to the polymer surface in admixture applications.

In a further aspect, the invention provides compositions of a base polymer in admixture with a bioactive fluoroalkyl surface modifier (BFSM), as hereinabove defined, preferably in the form of a shaped article.

Examples of typical base polymers of use in admixture with aforesaid BFSM according to the invention, includes polyurethanes, polysulfones, polycarbonates, polyesters, polyethylene, polypropylene, polystyrene, polysilicone, poly(acrylonitrile-butadienestyrene), polybutadiene, polyisoprene, polymethacrylate, polyvinylacetate, polyacrylonitrile, polyvinyl cloride, polyethylene terephtahate, cellulose and other polysacharides. Preferered polymers include polyamides, polyurethanes, polysilicones, polysulfones, polyolefins, polyesters, polyvinyl derivatives, polypeptide derivatives and polysaccharide derivatives.

The admixed compositions according to the invention may be used as a surface covering for an article, or, most preferably, where the composition comprises a base polymer of a type capable of being formed into 1) a self-supporting structural body, 2) a film; or 3) a fiber, preferably woven or knit. The composition may comprise a surface or in whole or in part of the article, preferably, a biomedical device or component thereof; an affinity column for pharmaceutical or biomolecule purification, or microfilm form for diagnostic and bio-sensor applications.

In a preferred aspect, the invention provides an admixed composition, as hereinabove defined, comprising in admixture either a polyurethane, polysilicone, polyester, polycarbonate polysaccharide with a compatible BFSM, in a surface modifying enhancing amount of preferably 0.5–10 w/w %, more preferably 1–5 w/w %, more preferably 2–10 w/w % of the resultant admixed composition. In the case of a polyurethane base, it should have a molecular weight of at least 1.05 times the molecular weight of the BFSM.

Thus, this invention, in one aspect, defines a family of novel bioactive fluoroalkyl surface modifiers that have fluorinated tails at each end of the molecule and bioactive molecules grafted to [linkB] segments within the chain of the surface modifier. The centre of the BFSM is tailored to be compatible with the base polymer substrate to which it is added.

The BFSMs, according to the invention, are synthesized in a manner that they contain a base polymer compatible segment, terminal hydrophobic fluorine components which are non-compatible with the base polymer and a bioactive moiety containing biochemical function with either inherent anti-coagulant, anti-inflammatory, anti-oxidant, anti-microbial potential, cell receptor ligands, e.g. peptide ligands and bio-adhesive molecules, e.g. oligosaccharides, oligonucleic acid sequences for DNA and gene sequence bonding, phospholipid head groups to provide cell membrane mimics, or a precursor of the bioactive moiety.

The base polymer compatible segment of the BFSM i.e. the [oligo] [linkA] and [linkB] segments is selected to provide an anchor for the BFSM within the base polymer substrate upon admixture. While not being bound by theory, it is believed that the oligomeric fluorine tails, which are not miscible with the base polymer, provide a significant driving force for carrying the the BFSM towards the surface, with the terminal ends of the BFSM oriented outwards of the surface. The latter process is believed to be driven by the thermodynamic incompatibility of the fluorine tails with the base polymer substrate, as well as the tendency towards establishing a low surface energy at the mixture's surface. When the balance between anchoring and surface migration is achieved, the BFSM remains stable at the surface of the polymer, while simultaneously altering surface properties. Since the biologically active compound is coupled immediately adjacent to the $\alpha$-$\omega$ fluorine tails of the BFSM in the linkB segment, they will also be preferentially delivered to the surface of the base polymer substrate.

I have found that the utility of the additives of the invention versus other known macromolecular additives or drug polymer conjugates, lies in:

1) BFSMs are relatively low molecular weight compounds of <15,000, which allows them to more readily diffuse among the macromolecular polymer chains of the base material;
2) BFSM can modify surfaces at less than 5 wt % of the BFSM relative to the weight of the base polymer to which they are added. This is an important attribute because it minimizes significant bulk changes to the base materials to which BFSM is added, and therefore, allows for a specific biological activity to be present at the surface, while the bulk base material performs its intended task. For example, if a 3-dimentional porous matrix is desired for a tissue engineered structure with low-swelling function, such a material could not be constructed of traditional biogel polysaccharide matrices. However oligomeric saccharides with cell adhesive character may be synthesized into a BFSM for delivery to the surface of a low swelling material such as a L-poly-lactic acid. In this system, surface bio-activity can be tailored separately from bio-resorbing rates for the base polymer. This is often desired in the case where mechanical function is desired to remain relatively stable over the tissue integration period.
3) BFSM simultaneously establishes a fluorocarbon segment at the surface and a biological or pharmaceutical agent pendent adjacent to the fluorocarbon segment chemistry. The fluorocarbon base provides in terms of surface energy, a relatively neutral surface, which does not promote strong cell adhesion and minimizes protein activation. This feature is strategic since relative to the remainder of the surface, it permits the [Bio] component adjacent to the fluorocarbon base to have a specific cellular or biomolecular interaction with the intended target i.e. for example, platelet, bacteria, thrombin, and the like. The surface modification achieved by the simultaneous combination of surface passivation i.e. $\alpha$-$\omega$ fluorine tails and target biological function has not been previously achieved and/or demonstrated with any other family of surface amphipathic polymeric type surface modifying macromolecules or drug polymer conjugate.
4) The [linkB] molecule contains one or several functional groups for attachment of the [Bio] component. Depending on the nature of the [linkB] functional group(s), the [Bio] component may be rendered stable for local surface function or hydrolysable for the delivery of Bio components remote from the polymeric implant surface. The introduction of such capabilities has not been previously achieved and/or demonstrated with any other family of surface amphipathic polymeric type surface modifying macromolecules.
5) All BFSMs use similar fluorocarbon oligomers to drive the BFSM to the surface. This permits the delivery of different types of [Bio] components to the surface by simply addition of a blend of different BFSM additives to the desired polymer matrix. For example, it may be desired for a blood contact material to deliver an antibiotic, anticoagulant and a peptide ligand to the surface of a polymer. The former would provide an acute defense against initial bacterial challenges, the anticoagulant could control acute thrombogenenic events and the peptide ligand may provide a longterm binding site for re-endothelializing a surface. This represents a controlled multi-functional surface modification not previously achieved and/or demonstrated with any other surface modification technology in the biomedical and biotechnological discipline.
6) Since a BFSM has the potential to migrate to the surface during processing i.e. film forming, extrusion, fibre forming, and the like, the present invention provides for the elimination of post-processing steps for introducing bio-active molecules at the surface, as is required with other techniques in the field i.e. radiation grafting polymerization; chemical coating, solvent coating; electron radiation; plasma polymerization or deposition; and the like. The provision for such capabilities represents surface modification approach not previously achieved and/or demonstrated with any other surface modification technology in the biomedical and biotechnological discipline.

The surface modifying agents according to the invention significantly alter the surface chemistry and biochemistry of, for example, segmented polyurethanes, i.e. for example, a BFSM containing a natural anti-oxidant e.g. vitamin-E can migrate to the surface of the polymer mixture and exhibit a new hydrophobic surface. The advancing contact angle, which is a measure of the surface's hydrophobic components for the examples, hereinafter described, shows significant increases and parallel values with those of typical fluoropolymers i.e. 116° for the advancing contact angle of Teflon® fluorocarbon. The advancing contact angle measurement therefore becomes an effective tool for assessing the extent of change introduced when the fluorine segments of the BFSM direct the molecule to the surface. A further confirmation of the specific affinity of the BFSM at the surface is to assess elemental change, with fluorine being an easy marker. X-ray photo-electron spectroscopy is an effective tool for identifying changes in elemental types and distributions within the upper 10 nm of the surface. For the polyurethane examples herein described, it is found that a 5 wt % of the BFSM relative to the polymer can have an atomic percentage of fluorine in excess of 40%, whereas the background fluorine values for the non-modified polyurethane is less than the detection limits of 1–2 atomic %.

The presence of the drug, adjacent to the [fluoro] segment of the BFSM at the surface, can also be assessed by changes in advancing contact angles, as well as by changes in the specific bio-activity at the surface. The introduction of a typical organic, i.e. carbon/oxygen/nitrogen/hydrogen atom-containing based drug adjacent to the surface fluorine, reduces the advancing contact angle of the surface, relative to that of a surface with surface modifiers only containing the terminal fluorine groups. Specific activity can be assessed based on the units of measure for a particular molecules bio-function. For instance, for a BFSM containing an anti-coagulant, such as heparin, the activity can be measured by determining the deactivation of thrombin in the presence anti-thrombin, while the activity of vitamin-E can be measure by the surfaces ability to quench free radicals generated by oxidants.

The BFSM's are, for example, of use with, but not limited to, linear or crosslinked polysilicone, polyester, polyurethane, polyethersulfone, polycarbonate, polyolefin and polyamide materials. By tailoring the central portion of the BFSM, the present invention may be applied, inter alia, to a wide range of polymer materials, which include polymers synthesized with reagents that are of common knowledge in the field of segment polyurethanes. This class of polymers is composed of heterogeneous compounds in which, quite often, the urethane groups themselves only make up a fraction of the dominant functional linkages within the macromolecular chains. These include, but are not limited to, various diisocyanates, oligomeric precursor components and low molecular weight chain extender components.

Reagents Used For The Synthesis Of Urethane Based Polymers

| Diisocyanates | Oligomeric precursor diol and diamine components | Chain extenders |
|---|---|---|
| -2,4 toluene diisocyanate | Polycarbonate | -Butane diol |
| -2,6 toluene diisocyanate | Polysiloxanes | -Ethylene diamine |
| methylene bis (p-phenyl) diisocyanate | Polydimethylsiloxanes | -Hexamethylene diamine |
| -1,5 naphthalene diisocyanate | Polyethylene-butylene | -Hexamethylene dicarboxylic acid |
| -3,3' bi-toluene diisocyanate | Polyisobutylene | -Lysinate |
| -lysine diisocyanato esters | Polybutadienes | -Hexane diol |
| -1,6 hexane diisocyanate | Polyesters | -2,5 diaminobenzenesulfonic acid |
| -1,12 dodecane diisocyanate | Polyethersulfones | -4,4'diamino 2,2'- biphenyl disulfonic acid, |
| -isophorone diisocyanate | Polyurethane | -1,3-diamino 2-hydroxypropane |
| -cyclohexyl diisocyanate | Polyurea | -N-(2-aminoethyl)-3- aminopropane sulfonate |
| -bis methylene di (cyclohexyl isocyanate) | Polyamide | -Dihydroxy vinyl derivatives |
| -trimethyl-1,6 diisocyanatohexane | Polyalkylene oxide | -Dihydroxy diphenyl-sulfone |
| | Polyvinyl derivatives | -Hexamethylene diol |
| | Polypeptide derivatives | -1,5 pentanediol |
| | Polysaccharide derivatives | -2,2-dimethyl-1,3 propanediol |
| | Polypropylene oxide | -1,2-diamino-2 methylpropane |
| | Polyethylene oxide | -3,3,-diamino-N-methyldipropylamine |
| | Polytetramethylene oxide | -1,4 diaminobutane |
| | Polyethylenebutylene | -1,7 diaminoheptane |
| | | -1,8 diaminooctane |
| | | -glutary dichloride |
| | | -adipoyl dichloride |

There are no restrictions on the specific stoichiometry of the reagents used in the synthesis of the BFSM. With the exception of the [Bio] components, there is no restriction in the manner in which the reagents are added to each other, the temperature, pressure or atmosphere under which they are synthesized or the use of catalysts in their reaction. However, [oligo] components are of relatively short length in terms of the repeating unit or units, and are generally less than about 20 monomeric units and of molecular weights less than 5000. Typically, linkA molecules have molecular weights ranging from 40 to 700 and must have difunctionality to permit coupling of two [oligo] units. Typically, [fluoro] units can have molecular weights ranging from 100 to 1500; and linkB molecules have molecular weights ranging from 40 to 700. [Bio] units have molecular weights ranging from 40 to 5000, but may be higher if they do not inhibit transport of the BFSM to the surface of the material being used to form an intended shaped article. It is not desirable to simultaneously synthesize a BFSM additive with the base polymer is which they are admixed, since the synthesis of the BFSM additive may be sensitive to reaction conditions of other polymers. As well, it is not desirable to carry out the Bio component coupling at the same time as reacting the other reagents in the production of the BFSM, since the Bio compiling reaction may be sensitive to reaction conditions. The BFSM as an additive may be added to a base polymer synthesis reaction, in such a manner as to incorporate the BFSM additive into the base polymer substrate, prior to the final work-up of the polymer substrate.

In order to illustrate the design of BFSM additives for common polymers as the base polymer, and to describe the rationale for the selection of the BFSM candidates, five polymers were used as representative compounds compatible with the list of reagents given, hereinbefore. One material is MED10-6640 silicone dispersion Pt catalyst, polydimethylsiloxane elastomer from Nusil Silicone Technology. Another is a polycarbonate based polyurethane (HDI/PCN/BD) synthesized from 1,6 hexamethylene diisocyanate, polycarbonate of molecular weight 970, butane diol and dibutyltin dilaurate catalyst. The remaining three polymers were polyethersulfone (PES 4100P™) from ICI chemicals, polypropylene and nylon 6,6 (Aldrich). Thus, the reagents and stoichiometry used in the synthesis of the BFSM according to the invention for these particular materials favour chemical compatibility with the base, i.e. have an appropriate arrangement of polar versus non-polar character. Clearly, a BFSM based on a polyamide [oligo] component would not be chemically compatible with a polysiloxane base elastomer. A balance between chemical compatibility with the base polymer and specific migration towards the surface of the base polymer is preferably achieved by keeping the molecular weight of the BFSM between the ranges of 500 to 15,000. If the central component of the BFSM, made up of [oligo], [linkA] and [link B] segments, is too large, for example, typically >30 times that of the [fluoro] segments, it is difficult for the surface driving terminal [fluoro] segment to effectively attain residence at the surface of the base polymer during the time of device processing. Stronger interactions resulting from dispersion and dipole/dipole forces between the BFSM's central portion, composed of [oligo], [linkA] and [link B] segments, and the base polymer results in overall lower molecular weights for the BFSM. The latter also favor surface migration of the BFSM. Therefore, control of the molecular weight in the synthesis of an effective BFSM is highly desirable in its ability to modify the surface chemistry of a polymer substrate.

The BFSM may be synthesized using a multi-functional linkA molecule, a multi-functional oligo molecule, a multi-functional linkB molecule, a molecule and a Bio molecule having at least a functional component that can be covalently coupled to the BFSM via the secondary function of the [linkB] segment. The linkA and the primary function of the linkB molecules are preferably, but not so limited, to be di-functional in nature, in order to favour the formation of a linear BFSM. Linear, as apposed to branched or crosslinked BFSMs, have better migration properties within the base polymers, since interactions resulting from dispersion and dipole/dipole forces are reduced. Preferred linkA molecules for biomedical and biotechnology applications are diisocyanates: for example, 2,4 toluene diisocyanate; 2,6 toluene diisocyanate: methylene bis (p-phenyl) diisocyanate; lysine diisocyanate esters; 1,6 hexane diisocyanate; 1,12 dodecane diisocyanate; bis methylene di (cyclohexyl isocyanate); trimethyl- 1,6 diisocyanatohexane. The molecular weights of the [oligo] groups are between 200 to 5000, but preferably have molecular weights of less than 3500. Synthesis of the central portion of the BFSM can be carried out by classical reactions using the desired combination of reagents.

In the final step, a Bio component is coupled to the secondary function of the link B segment. These reactions are typically carried out by classical nucleophilic reactions and may involve a pre-activation of the secondary site on the link B component. For example, the coupling of the terminal hydroxy group in vitamin-E, a typical Bio component to an ester linkage of a lysine methyl ester segment (typical link B component) within the BFSM's central portion, requires the conversion of the ester to a carboxylic acid which can then undergo a condensation reaction with the hydroxyl of the vitamin-E molecule to yield the final BFSM. The latter coupling reaction can be further facilitated by incorporating better leaving groups than "—OH" on the carboxylic acid. Examples of preferred reagents include oxalyl chloride, ethylchlorofonnate, 1-ethyl-3-(3-dimethylamino-propyl carbodiimide (EDC)/N-hydroxysuccinimide (NHS) and N,N' carbonyldiimidazole. As well, it may be desired to have the drug extended out from the backbone of the BFSM to facilitate its biological role. This is typically done for anticoagulants like heparin, prior to their grafting onto substrates. Reaction of these particular components with a secondary carboxylic acid groups of the BFSM's link B segments simply extends the secondary function of the BFSM for subsequent coupling of a drug molecule such as vitamin-E and GHG (the genetics housekeeping probe that is expressed in all cells to provide basic function needed for survival) procured from ACGT corp., Toronto ON

```
5'p ATA CTG AGA TGG GTG CCG TTC TAT GAC TCT ACC
   CAC GGC AAG TTC AA-OH-5' (SEQ ID NO: 1).
```

BFSMs can be synthesized with different components and stoichiometry. Prior to synthesis, the linkA and linkB molecules are, preferably, vacuum distilled to remove residual moisture. Bio compounds are dessicated to remove all moisture. Oligo components are degassed overnight to remove residual moisture and low molecular weight organics. Where BA-L is used as the fluoroalcohol, for example, this reagent is fractionated into three fractions to reduce the distribution of molecules with different "m" values. This reduces the selective reaction of a fluoro-alcohol of a particular "m" value over another, to provide for more control in the desired final product. The BA-L fractions are characterized as (i) a first fraction, herein called "L" fraction which is a clear liquid distilled at 102° C. and atmospheric pressure; (ii) a second fraction referred to as "I" fraction, which is a white semi-solid material, distilled between 70 and 80° C., under a vacuum of 0.01 mm Hg pressure; and (iii) a last fraction referred to as "H" fraction and is distilled between 80 and 100° C., under a vacuum of 0.01 mm Hg and recovered as a very pale yellow solid. The selection of these fractions is somewhat arbitrary and it will be apparent to those skilled in the art that different fractions can be selected to alter the nature of the BFSM in order to tailor the material for specific applications with base polymers.

While reactants can be reacted in the absence of solvents if practical, it is preferable to use organic solvents compatible with the chemical nature of the reagents, in order to have good control over the characteristics of the final product. Typical organic solvents, include, for example, dimethylacetamide, acetone, tetrahydrofuran, ether, chloroform, dimethylsulfoxide and dimethylformamide. A preferred reaction solvent is N,N-dimethyleacetamide (DMAC, Aldrich Chemical Company, Milwaukee, Wis.).

In view of the low reaction activity of some diisocyanates, e.g. LDI and HDI, with oligo precursor diols, a catalyst is preferred for the synthesis. Typical catalysts are similar to those used in the synthesis of urethane chemistry and, include, dibutyltin dilaurate, stannous octoate, N,N' diethylcyclohexylamine, N-methylmorpholine, 1,4 diazo (2,2,2) bicyclo-octane and zirconium complexes such as Zr tetrakis (2,4-pentanedionato) complex.

In the first step of the preparation of a BFSM, for example, the linkB and linkA (optionally) reactant molecules are added to the oligo component and, optionally, catalyst to provide the "central portion" of the BFSM. Subsequently, the fluoro reactant component is added to the central portion and, generally, the mixture is allowed to react overnight. The product is precipitated in distilled water or a mixture of distilled water with methanol or ether. The latter step removes any residual fluoro reactant compound, while the product is dried under vacuum at 60° C. Subsequent steps require activation of the secondary function on [linkB]. In a preferred case, this entails hydrolysis of a protective ester group on molecules such as LDI. This is achieved by dissolving the BFSM precursor in DMF and adjusting the acid content in the DMF solution, using an aqueous 1.0 N hydrochloric acid solution, to a pH reading of 1.5 on a pH meter. The solution temperature is then raised to 45° C. and maintained at this temperature for 4 hours in order to permit the hydrolysis of the pendant ester groups. A base catalysed hydrolysis is also an option for de-esterification. The BFSM precursor is then precipitated in 1 M aqueous KCl, washed in distilled water and dried under vacuum at 60° C. for 48 hours. The acid group of the BFSM precursor is then reacted with either oxalyl chloride, N,N' carbonyldiimidazole and 1-ethyl-3-(3-dimethylamino-propyl carbodiimide (EDC)/N-hydroxysuccinimide (NHS) or other agents to introduce a good leaving group on the acid. This step permits for an efficient nucleophilic reaction to take place with the Bio component. In the preferred case oxalyl chloride is mixed with a solution of the acidified BFSM precursor in distilled DMF, in a nitrogen atmosphere. The solution is first cooled to 5° C. with an ice bath and oxalyl chloride is added stoichiometrically to the amount of acid groups. Triethylamine is added to scavenge free HCl which is generated as a by-product. The latter reaction step produces an acid chloride BFSM precursor which is now ready to react with hydroxyl or amine groups on the Bio component. This could be the hydroxyl on vitamin-E, heparin or other oligosaccharides, hydrocortisone; the amine on norfloxacin, ciprofloxacin, phosphatidylcholine and phosphorylcholine derivatives, terminal amine of a peptide sequence, hydroxyl or amine of an oligonucleotide; or the amino/hydroxyl terminals of an ethylene oxide spacer group if so desired. The Bio molecule is dissolved into a suitable solvent, preferably DMF and added to the acid chloride BFSM precursor reaction mixture and the solution is allowed to react overnight at 20° C. The final BFSM is precipitated in a mixture of ethanol/1 M aqueous KCl solution (30/70 vol %). The precipitated polymer is then washed three times in an 80/20 vol % ethanol/water mixture. Following washing, the material is dried under vacuum.

Fabrication of Product:

The BFSM's are admixed with suitable amounts of base polymers in the fabrication of article products. The BFSM may be admixed with, for example, polyurethane base polymers by; 1) compounding methods for subsequent extrusion or injection molding or articles; 2) co-dissolving the polyurethane and BFSM into a solvent of common compatibility for subsequent casting of an article in a mold or for spinning fibers to fabricate an article; 3) wetting the surface of a polyurethane with a solution of BFSM in solvent of common compatibility with the polyurethane to which the BFSM solution is being applied; or 4) in admixture with a curable polyurethane, for example, 2 part curing system such as a veneer.

The invention, thus, provides in one aspect a series of novel polymeric additives, termed bioactive fluoroalkyl surface modifiers (BFSM) possessing intramolecular properties of biological activity endowed by distinct chemical functional groups and an affinity for polymeric surfaces endowed by polyfluoro oligomeric groups. When used in admixture with, for example, a polyurethane, the BFSMs establish a fluorocarbon base at the surface with a biological or pharmaceutical agent pendent adjacent to the fluorocarbon. The fluorocarbons provide a relatively neutral surface, in terms of surface energy, which does not promote strong cell adhesion, minimizes protein activation, and reduces biodegradation. This surface arrangement of fluorine chemistry is strategic, since in relation to the remainder of the surface, it permits the [Bio] component adjacent to fluorocarbon base to have a very specific cellular or biomolecular interaction with the intended target (i.e. platelet, bacteria, thrombin, etc.). When different BFSM's are combined in admixture with the base polymer it permits for the development of a multifunctional surface, thus simultaneously addressing multiple issues of stability and bio-compatibility (e.g. coagulation, infection, inflammation, cell migration) related to implant materials. The BFSM's are copolymers or terpolmers that have the ability to alter the surface chemistry and biochemistry and, hence, surface properties of a polymer and are synthesized in such a manner that (i) preferably, they have a lower molecular weight than the base material i.e. the polymer that requires the surface modification, (ii) they contain a surface active segment containing α-ω terminal polyfluoro oligomeric groups and (iii) finally pendent drug or biologically active agents ([Bio]) that can be coupled to [linkB] components of the BFSM, for providing articles having bioactive surface properties, particularly for use in medical devices, promoting cell function and regulation, tissue integration, pro-active blood compatibility and specifically anti-coagulant/platelet function, biostability function, anti-microbial function and anti-inflammatory function, or for use in the biotechnology sector for improving affinity column chromatography systems or promoting surface catalytic reactions, or a biosensor and bio-diagnostic substrate.

Products such as medical devices formed of the admixed composition of the invention, have their surfaces modified as a result of the selective migration and interfacial localization of the low molecular weight oligomers containing pendent molecules with specific potential biological activity, carbon/fluorine segments and non-carbon/fluorine segments within the same molecule, such that the carbon/fluorine segments are terminal in the macromolecule and selectively reside at the material/environment interface, and such that the [Bio] moieties are coupled immediately adjacent, via the [linkB] segments, to the terminal carbon/fluorine segments of the macromolecule so that they also selectively reside at the surface of the material, while the non-carbon/fluorine segments are remote from the macromolecule's terminal position, but reside within the upper surface of the product.

BFSMs, thus, contain, by synthesis through precursor-containing linkable-moieties such as hydroxyl, carboxylic acid and ester and preferably as pendent biological agents such as, for example, anti-inflammatory, agents such as, for example, non-steroidal-diflunisal via precursor hydroxyl, ibuprofen via carboxylic acid, naproxen via carboxylic acid, steroidal-hydrocortisone via hydroxyl, prednisolone via non-ring anti-coagulant agents, such as, heparin; anti-microbial agents, such as, fluoroquinolones such as norfloxacin, ciprofloxacin, sparfloxacin and trovafloxacin; and cell receptor ligands, such as, RGD integrin binding domain for a host of cells membranes, including macrophages, platelets, and the like, PHSRN (SEQ ID NO: 2), YRGDG (SEQ ID NO: 3), and RGDSPASSKP (SEQ ID NO: 4) amino acid sequences to promote cell activation and spreading; oligosaccharides, such as heparin sulfate, hyaluroic acid, dermitan sulfate, chondroitin 6-sulfate, keratan sulfate and heparin sulfate, for cell adhesion character in tissue engineering applications; oligonucleotides for binding DNA fragments and coupling of genes for bio-diagnostics, which this is best achieved with adapter sequences that have both strands of the cDNA that can protect the amine groups of the repeating nucleotides during coupling via the 5' hydroxyl of the terminal nucleotide. Examples include aforesaid GHG and phospholipid head groups such as phosphatidylcholine and phosphorylcholine derivatives, for mimicking cell membranes. As well, BFSMs, thus, contain, preferably as α-ω terminal polyfluoro oligomeric groups, fluoropolymeric segments comprising a sequential group of carbon atoms containing fluorine atoms and constituting an oligomeric chain. Preferred perfluorinated alcohols of use in the practice of the invention are those of the general formula $CF_3(CF_2)_nCH_2CH_2OH$, having a linear alkyl chain, wherein n is 5–9, most preferably $C_8F_{17}CH_2CH_2OH$. These monomers are commercially available as homologous mixtures having varying degrees of fluoroalkane chain lengths. One such preferred mixture available under the name BA-L (Dupont trade marks-obtained from Van Waters and Rogers, Montreal, Canada) has an average molecular weight of 443; fluorine content of 70%; S.G. 1.5 @ 30° C. thickening point <25° C. and a boiling range of 102–175° C. @ 50 mm Hg.

BRIEF DESCRIPTION OF THE DRAWINGS

In order that the invention may be better understood, preferred embodiments will now be described by way of example only, with reference to the accompanying drawings wherein.

DETAILED DESCRIPTION OF PREFERRED EMBODIMENTS

Figure 1:
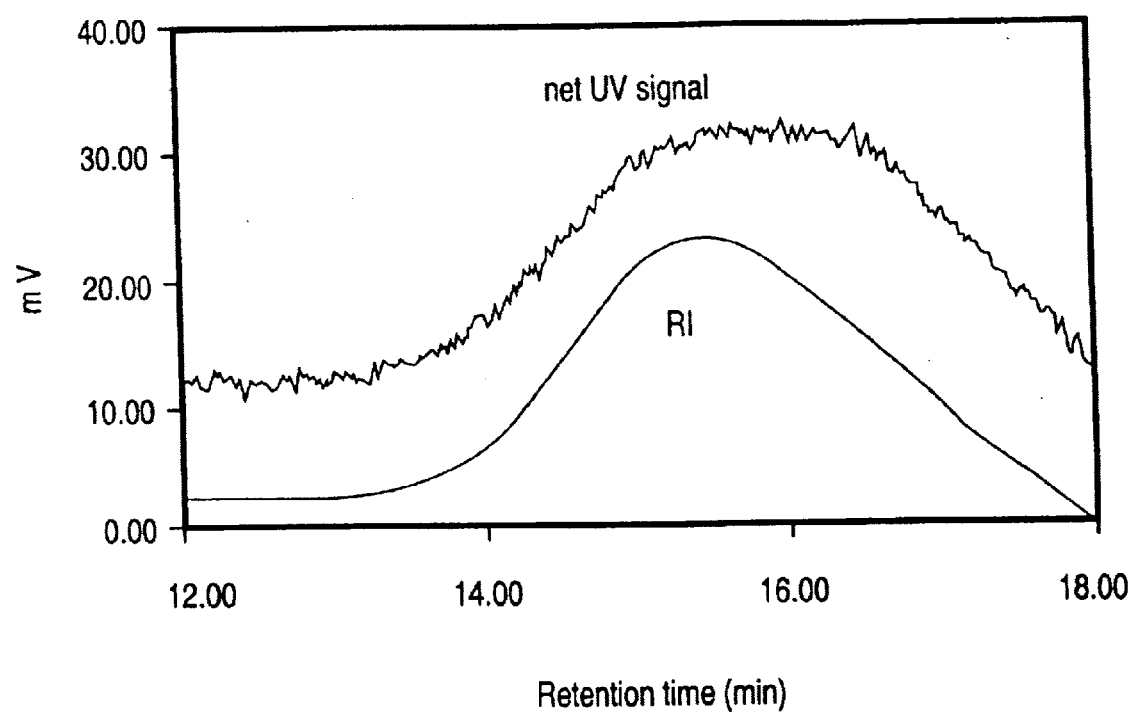
FIG. 1 is a gel permeation chromatography analysis of LDI/PCN/I/VITE.
Figure 2:
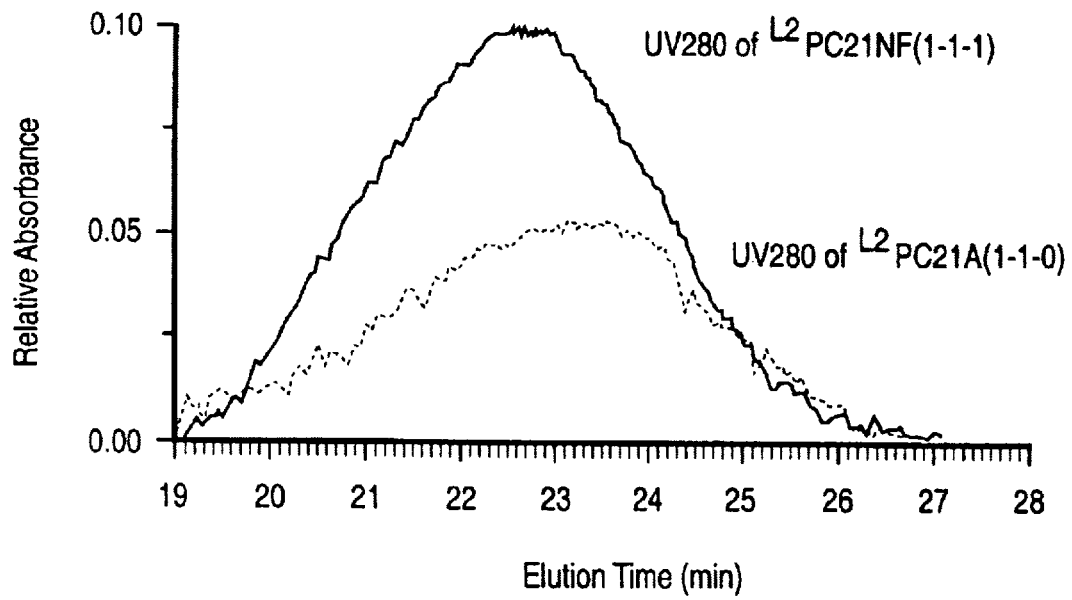
FIG. 2 is a gel permeation chromatography analysis of a LDI/PCN/I/NORF.

In these examples, the following acronyms are used.

| | |
|---|---|
| LDI | (lysine diisocyanate) |
| HDI | (1,6 hexamethylene diisocyanate) |
| DABS | (2,5 diaminobenzenesulfonic acid) |
| PCN | (polycarbonate diol) |
| PPO | (polypropylene oxide diol) |
| MDI- | methylene diphenyl diisocyanate |
| HMDI- | methylene dicyclo hexamethylene diisocyanate |
| PEO | polyethylene oxide |
| PTMO | polyethylene tetramethylene oxide |
| PCN | polycarbonate diol |
| PDMS | (polydimethylsiloxane-bis (3-aminopropyl) terminated) |
| PHE | (amine terminated oligo-phenylalanine) |
| PEB | (polyethylene-butylene co-polymer diol) |
| THDI | (trimethyl-1,6 diisocyanatohexane) |
| DPS | (dihydroxy diphenylsulfone) |
| PD | (1,5 pentanediol) |
| VITE | (vitamin-E) |
| HEP | (heparin) |
| HYA | (hyaluronic acid) |
| GGRGD | (glycine/glycine/arginine/glycine/aspartic acid peptide sequence, supplied by analytical laboratory at the Hospital for Sick Children) |
| DABS | |
| NORF | (Norfloxacin) |
| GPC | (L-α-glycerophosphorylcholine) |
| HC | (hydrocortisone). |
| MED10-6640 | (polydimethylsiloxane elastomer) |
| HDI/PCN/BD | (segmented polyurethane) |
| PES 4100P | (polyethersulfone) |
| PP | (polypropylene) |
| DMAc | (dimethylacetamide) |
| DMF | (dimethylformamide) |
| BA-L | (fluoro-oligomer), fractions I and H, chain length of I < H |
| GHG | (genetics housekeeping prope that is expressed in all cells to provide basic function needed for survival) procured from ACGT corp., Toronto ON |

5'p ATA CTG AGA TGG GTG CCG TTC TAT GAC TCT ACC

CAC GGC AAG TTC AA-OH-5' (SEQ ID NO: 1)

BFSM's were synthesized using classical urethane reactions for the synthesis of the central portion of the BFSM, end-capping reactions for coupling of the terminal [fluoro] components, and classical nucleophilic reactions for coupling of the [Bio] components. The reagents used for the synthesis of BFSM's included linkB molecules and linkA molecules, LDI, HDI, DABs, [oligo] PCN, PPO made from mol. weight=425, Aldrich Chemical Company), amine terminated PHE (Sigma Chemical, carboxylate terminal converted to an amine), PDMS (η=50 cst and approximate molecular weight of 2600, Aldrich Chemical Company)), PEB (HO——[(CH$_2$CH$_2$)$_x$——(CH$_2$CH(C$_2$H$_5$)$_y$—]——OH of molecular weight 2500 (Aldrich Chemical Company)); and oligomeric polyurethanes, THDI-DPS and HDI-PD, synthesized from THDI/DPS, and HDI with PD; [fluoro] components included the I and H fractions of the fluoroalcohol BA-L (Dupont trade mark); [Bio] components consisting of VITE (vitamin-E, Sigma Chemicals, St-Louis, U.S.A.), HEP (heparin), GPC (L-α-glycerophosphorylcholine, Sigma, U.S.A.), NORF (Sigma Chemicals, St-Louis, U.S.A.), GGRGD, Sigma Chemicals, St-Louis, U.S.A.), HC (Sigma Chemicals, St-Louis, U.S.A.), HYA (Genzyme corp, Cambridge Mass.), GHG (genetics housekeeping prope, ACGT corp., Toronto ON 5'p ATA CTG AGA TGG GTG CCG TTC TAT GAC TCT ACC

CAC GGC AAG TTC AA-OH-5' (SEQ ID NO: 1)

Where appropriate all isocyanate reactions were catalysed with DBTL (dibutyltin dilaurate). Where appropriate oxalyl chloride or N,N' carbonyldiimidazole were used to generate leaving groups for the coupling of the [Bio] molecules. Where appropriate, polyethylene oxide diamine (n=50, Aldrich Chemical Company) as used as a space molecule for the [Bio] components.

Base polymers were either synthesized or obtained commercially. For example, one material is MED10-6640 Silicone dispersion Pt catalyst, polydimethylsiloxane elastomer from Nusil Silicone Technology. Another is a HDI/PCN/BD (polycarbonate based polyurethane) synthesized from 1,6 hexamethylene diisocyanate (Aldrich Chemical Company), polycarbonate (molecular weight 970, Stahl Corp., Germany), butane diol (Aldrich Chemical company) and dibutyltin dilaurate catalyst (Aldrich Chemical Company). The remaining two polymers were PES 4100P (polyethersulfone) from ICI chemicals, and PP (polypropylene) obtained from Aldrich Chemical Company, Milwaukee, Wis.

Gel permeation chromatography was used to define the distribution of [Bio] the moiety within the BFSM and to estimate relative molecular weights of the BFSM. Elemental analysis was carried out to define fluorine content in typical BFSM.

Characterization of BFSM located at the surface of the base polymer substrates was demonstrated using X-ray photoelectron spectroscopy (measuring chemical composition) and contact angle analysis (measuring wetability).

Chemical and physical changes in the base polymers, with and without BFSM's, following exposure to biological environments was monitored by scanning electron spectroscopy (SEM), attenuated transmission reflectance Fourier transform infrared spectroscopy (ATR-FTIR)

Bio-activity of a surface delivered BFSM is demonstrated for the anti-oxidant/anti-inflammatory vitamin-E using a taurine-iodide colometric method to measure oxidant consumption.

Examples 1–16 are examples of BFSMs, examples 17 and 18 are examples of the BFSM in admixture with substrates and demonstrate the presence of bio-active function at the surface, example 19 demonstrates the effect of the BFSM altering providing enhanced biocompatibility with a biological environment. Example 20 demonstrates the use of BFSMs with base polymers in medical devices, and in non-medical applications.

EXAMPLE 1

LDI/PCN/I/VITE is an example of a BFSM according to the invention which contains a high fluorine content and a pendent vitamin-E molecule coupled adjacent to the fluorine tails of the BFSM such that the molecule can reduce the inflammatory stimulated response of the oxidant HOCl (hypochlorous acid). In addition, this BFSM can contribute to enhancing the biocompatible nature of the polymer surface, in which the BFSM is added, with the interfacing biological environment, specifically reducing the ability of inflammatory cell derived oxidants to degrade polymer surfaces. LDI/PCN/I/VITE was synthesized with lysine diisocyanate as both the linkA and linkB molecules, polycarbonate diol (molecular weight of 970), (PCN) was use as the oligo component, fraction (I) of the fluoroalcohol BA-L was used as the [fluoro] component and vitamin-E was used as the [Bio] component. This BFSM will be referred to as. LDI/PCN/I/VITE, throughout this text. The conditions of synthesis for this reaction are as follows.

5 grams of PCN were reacted with 1.9 grams of LDI for two hours and then 3.2 grams of "I" were added to the reaction. The mixture was reacted in a nitrogen atmosphere with 2.1 mg of the catalyst, dibutyltin dilaurate, in 65 mLs of dimethylacetamide (DMAc) and the reaction temperature was maintained between 60–70° C. The product of the latter reaction is precipitated in a mixture of distilled water with ether to remove residual [fluoro] compounds. The product of this step is dried under vacuum at 60° C. Activation of the methyl ester on [linkB] is carried out by hydrolysis of the protective ester group by dissolving the BFSM precursor in dimethylformamide (DMF) and adjusting the acid content in the DMF solution, using an aqueous 1.0 N hydrochloric acid solution, to a pH reading of 1.5 on a pH meter. The solution temperature is then raised to 45° C. for 4 hours. The acidified BFSM precursor is then precipitated in 1 M aqueous KCl, washed in distilled water and dried under vacuum at 60° C. for 48 hours. The acid group of the acidified BFSM precursor is then reacted with oxalyl chloride in a nitrogen atmosphere to introduce a chloride leaving group on the acid. The solution is first cooled to 5° C. with an ice bath and oxalyl chloride is added stoichiometrically to the amount of acid groups. Triethylamine is added stoichiometrically to the amount of acid groups to scavenge free HCl which is generated as a by-product. The latter reaction step produces an acid chloride BFSM precursor which is then reacted with the hydroxyl on the vitamin-E molecule. Vitamin-E was dissolved in DMF and added to the acid chloride BFSM precursor reaction mixture and the solution is allowed to react overnight at 20° C. The final BFSM is precipitated in a mixture of ethanol/1M aqueous KCl solution (30/70 vol %). The precipitated polymer is then washed three times in an 80/20 vol % ethanol/water mixture. Following washing the material is dried under vacuum. The final BFSM had a fluorine wt % of 14% which is quite typical of the selected stoichiometry which is anticipated to yield a fluorine content of approximately 12%, depending on the exact distribution of oligomers and the efficiency of product recovery. The polydispersity of the BFSM is 1.3. The theoretical molecular weight based on stoichiometry is approximately $3.0 \times 10^3$.

Vitamin-E is the only component in the BFSM which has a strong detectable absorbance at 320 nm in the UV range. Hence, its presence can be detected using a UV detector. FIG. 1 super-imposes the UV chromatogram for the BFSM with its universal gel permeation chromatography (GPC) curves using a universal refractive index detector. The latter detects the presence of all molecules because it has a dependence on mass of material present, eluting out of the GPC column at a specific time. Hence, a comparison of the two signals shows that the distribution of vitamin-E moieties is identical to the distribution of actual molecular weight chains, meaning that there was no preferential coupling of vitamin-E to low versus high molecular weight chains or vice-versa. This implies that the coupling of vitamin was uniform.

EXAMPLE 2

LDI/PTMO/I/HEP is an example of a BFSM with a stoichiometry that introduces a fluorine content of 5 wt % and pendent Heparin (molecule weight 3000, procured from Sigma Chemicals, St Louis) molecules coupled adjacent to the fluorine tails of the BFSM such that the molecule can catalyse the deactivation of thrombin (in key protein involved in the upregulation of clot formation) via antithrombin III (a key inhibitor of the clot forming process) at the surface of the polymer. In addition, this BFSM can contribute to enhancing the biocompatible nature of the polymer surface, in which the BFSM is added to, with the interfacing biological environment, specifically reducing the potential for blood to form uncontrolled thrombus growth on a biomaterial surface and generate subsequent embolization events. LDI/PTMO/I/HEP was synthesized with lysine diisocyanate as both the linkA and linkB reactants, polytetramethylene oxide diol (molecular weight of 1000) as the oligo component, fraction (I) of the fluoroalcohol BA-L was used as the fluoro reactant and Heparin sulfate was used as the [Bio] component. This BFSM will be referred to LDI/PTMO/I/HEP, throughout this text. The conditions of synthesis for this reaction are as follows.

10 grams of PTMO are reacted with 4.1 grams of LDI for two hours and then 11.7 grams (25% stoichiometric excess) of "I" were added to the reaction. The mixture was reacted in a nitrogen atmosphere with 50 mg of the catalyst, dibutyltin dilaurate, in 100 mLs of dimethylacetamide (DMAc) and the reaction temperature was maintained between 60–70° C. for 2.5 hours. The product of the latter reaction is precipitated in a mixture of distilled water with ether to remove residual fluoro reactant. The product of this step is dried under vacuum at 60° C. Activation of the methyl ester on [linkB] is carried out by hydrolysis of the protective ester group by dissolving the BFSM precursor in methanol and adding 1N NaOH in the MeOH solution, to a stoichiometric ratio +5% excess relative to the ester groups. The solution temperature was maintained at 20° C. for 18 hours. A 10% excess of 1N HCl solution (relative to the amount of base added in previous step) was added and stirred for 1 hour. The acidified BFSM precursor is then precipitated distilled water, washed and dried under vacuum for 24 hours. The acid group of the acidified BFSM precursor was then reacted with 1-ethyl-3-(3-dimethylamino-propyl carbodiimide (EDC) (in a 3:1 molar ratio of EDC:acid groups) and N-hydroxysuccinimide (NHS) (in a 1:1 molar ratio with EDC) in a nitrogen atmosphere to introduce a succinimide group on the acid. This solution reacts in DMF for 3 hours at 20° C. and the pH is maintained at 5.5. The latter reaction step produces a succinimide BFSM precursor which is then reacted with the hydroxyl or amines of the heparin molecule. Heparin is dissolved in 0.2 wt % aqueous NaCl solution and added to the succinimide BFSM precursor reaction mixture and the solution is allowed to react for 24 hrs at 20° C. The final BFSM is precipitated in a mixture of ethanol/1M aqueous KCl solution (30/70 vol %). The precipitated polymer is then washed three times in distilled water. Following washing the material is dried under vacuum. The fluorine wt % fluorine is anticipated to yield a fluorine content of approximately 5%, depending on the exact distribution of oligomers and the efficiency of product recovery. This fluorine content is above the typical cut-off value of 1% at which point selective migration of BFMS to the surface becomes compromised by competing dispersion and dipole-dipole interactions of the BFSM with the base polymer substrate. The theoretical molecular weight based on stoichiometry is approximately $8.5 \times 10^3$.

EXAMPLE 3

LDI/PCN/I/NORF is an example of a BFSM with a stoichiometry that introduces a fluorine content of approximately 10 wt % and pendent Norfloxacin molecules a broad spectrum fluoroquinolone anti-microbial agent moieties coupled adjacent to the fluorine tails of the BFSM such that the [Bio] component can provide an antimicrobial agent to the surface of the polymer to control the activity of bacteria, such as, for example, *P. aeruginosa* or *E. coli*, to minimize infection. In addition, this BFSM can contribute to enhancing the biocompatible nature of the polymer surface, in which the BFSM is added, with the interfacing biological environment, specifically reducing the potential for bacteria to form biofilms which ultimately leads to the removal of the implant. LDI/PCN/I/NORF was synthesized with lysine diisocyanate as both the linkA and linkB reactants, polycarbonate diol (molecular weight of 970) was used as the oligo component, fraction (I) of the fluoroalcohol BA-L was used as the fluoro component and Norfloxacin was the [Bio] component used as a representative of the fluoroquinolone family of anti-microbial agents. This BFSM will be referred to as LDI/PCN/I/NORF, throughout this text. The conditions of synthesis for this reaction are as follows.

5 grams of PCN are reacted with 1.9 grams of LDI for two hours and then 3.2 grams of "I" are added to the reaction. The mixture is reacted in a nitrogen atmosphere with 2.1 mg of the catalyst, dibutyltin dilaurate, in 65 mLs of dimethylacetamide (DMAc) and the reaction temperature was maintained between 60–70° C. The product of the latter reaction is precipitated in a mixture of distilled water with ether to remove residual [fluoro] compounds. The product of this step is dried under vacuum at 60° C. Activation of the methyl ester on [linkB] is carried out by hydrolysis of the protective ester group by dissolving the BFSM precursor in dimethylformamide (DMF) and adjusting the acid content in the DMF solution, using an aqueous 1.0 N hydrochloric acid solution, to a pH reading of 1.5 on a pH meter. The solution temperature is then raised to 45° C. for 4 hours. The acidified BFSM precursor is then precipitated in 1 M aqueous KCl, washed in distilled water and dried under vacuum at 60° C. for 48 hours. The acid group of the acidified BFSM precursor is then reacted with oxalyl chloride in a nitrogen atmosphere to introduce a chloride leaving group on the acid. The solution is first cooled to 5° C. with an ice bath and oxalyl chloride is added stoichiometrically to the amount of acid groups. Triethylamine is added stoichiometrically to the amount of acid groups to scavenge free HCl which is generated as a by-product. The latter reaction step produces an acid chloride BFSM precursor which is then reacted with the secondary amine of the norfloxacin molecule. Norfloxacin is dissolved in DMF and added to the acid chloride BFSM precursor reaction mixture and the solution is allowed to react overnight at 20° C. The final BFSM is precipitated in a mixture of ethanol/1M aqueous KCl solution (30/70 vol %). The precipitated polymer is then washed three times in an 80/20 vol % ethanol/water mixture. Following washing the material is dried under vacuum. The fluorine wt % fluorine is anticipated to yield a value of approximately 10%, depending on the exact distribution of oligomers and the efficiency of product recovery. This fluorine content is above the typical cut-off value of 1% at which point selective migration of BFMS to the surface becomes compromised by competing dispersion and dipole-dipole interactions of the BFSM with the base polymer substrate. The theoretical molecular weight based on stoichiometry is approximately $3.6\times10^3$.

Norfloxacin is the only component in the BFSM which has a strong detectable absorbance at 280 nm in the UV range. Hence, its presence can be detected using a UV detector. FIG. 2 super-imposes the UV chromatogram for the BFSM with its universal gel permeation chromatography (GPC) curves using a universal refractive index detector. The latter detects the presence of all molecules because it has a dependence on mass of material present, eluting out of the GPC column at a specific time. Hence, a comparison of the two signals shows that the distribution of Norfloxacin moieties is identical to the distribution of actual molecular weight chains, meaning that there was no preferential coupling of Norfloxacin to low versus high molecular weight chains or vice-versa. This implies that the coupling of Norfloxacin was uniform. In more detail, FIG. 2 shows gel permeation chromatography analysis of LDI/PCN/I/NORF ($^{L2}$PC21NF(1-1-1). The UV detector (280 nm) signal is matched to the polymer RI signal to confirm that norfloxacin is attached to the polymer chains of different size (i.e. retention time where longer times are shorter chains and early times are longer chains). Comparison of the UV absorbance for drug coupled BFSM ($^{L2}$PC21NF(1-1-1) with that of BFSM precursor ($^{L2}$PC21A(1-1-0) with no norfloxacin, based on the same amount of polymer injected for both sample.

EXAMPLE 4

LDI/PTMO/I/NORF is an example of a BFSM with a stoichiometry that introduces a fluorine content of approximately 10 wt % and pendent Norfloxacin moieties. This BFSM differs from the one in example 3 in that it was synthesized with PTMO rather than PCN, and the [Bio] coupling reaction was carried using a different reagent than oxalyl chloride to facilitate the introduction of Norfloxacin. As with example 3, this BFSM can contribute to enhancing the biocompatible nature of the polymer surface, in which the BFSM is added to, with the interfacing biological environment, specifically reducing the potential for bacteria to form biofilms which ultimately leads to the removal of the implant. LDI/PTMO/I/NORF was synthesized with lysine diisocyanate as both the linkA and linkB reactants, polytetramethylene oxide diol (molecular weight of 1000) (PTMO) was use as the oligo component, fraction (I) of the fluoroalcohol BA-L was used as the fluoro component and Norfloxacin was the [Bio] component. This BFSM will be referred to LDI/PTMO/I/NORF, throughout this text. The conditions of synthesis for this reaction are as follows.

10 grams of PCN are reacted with 4.1 grams of LDI for two hours and then 11.7 grams (25% stoichiometric excess) of "I" were added to the reaction. The mixture was reacted in a nitrogen atmosphere with 50 mg of the catalyst, dibutyltin dilaurate, in 100 mLs of dimethylacetamide (DMAc) and the reaction temperature was maintained between 60–70° C. for 2.5 hours. The product of the latter reaction is precipitated in a mixture of distilled water with ether to remove residual fluoro reactant. The product of this step is dried under vacuum at 60° C. Activation of the methyl ester on [linkB] is carried out by hydrolysis of the protective ester group by dissolving the BFSM precursor in methanol (MeOH) and adding 1N NaOH in the MeOH solution, to a stoichiometric ratio +5% excess relative to the ester groups. The solution temperature was maintained at 20° C. for 18 hours. A 10% excess of 1 N HCl solution (relative to the amount of base added in the previous step) was added and stirred for 1 hour. The acidified BFSM precursor was then precipitated distilled water, washed and dried under vacuum at 60° C. for 24 hours. The acid group of the acidified BFSM precursor was then reacted with 1-ethyl-3-(3-dimethylamino-propyl carbodiimide (EDC) (in a 3:1 molar ratio of EDC:acid groups) and N-hydroxysuccinimide (NHS) (in a 1:1 molar ratio with EDC) in a nitrogen atmosphere to introduce a succinimide group on the acid. This solution reacts in DMF for 3 hours at 20° C. and the pH is maintained at 5.5. The latter reaction step produces a succinimide BFSM precursor which is then reacted with the amine of the Norfloxacin molecule. Norfloxacin was dissolved in dimethylsulfoxide and added to the succinimide BFSM precursor reaction mixture and the solution was allowed to react for 24 hrs at 20° C. The final BFSM was precipitated in 1 M aqueous KCl solution. The precipitated polymer was then washed three times in distilled water. Following washing the material is dried under vacuum. The wt % fluorine is approximately 10%, depending on the exact distribution of oligomers and the efficiency of product recovery. This fluorine content is above the typical cut-off value of 1% at which point selective migration of BFSM to the surface becomes compromised by competing dispersion and dipole-dipole interactions of the BFSM with the base polymer substrate. The theoretical molecular weight based on stoichiometry is approximately $3.6 \times 10^3$. In a similar manner to the BFSM described in example 3, this SMM also shows a UV distribution in the gel permeation chromatograms, that overlaps that of the universal refractive index distribution. Again indicating efficiency coupling of the Norfloxacin all short and larger BFSM chains.

EXAMPLE 5

LDI/PTMO/I/GGRGD is an example of a BFSM with a stoichiometry that introduces a fluorine content of approximately 10wt % and pendent glycine-glycine-arginine-glycine-aspartic acid peptide sequences (a protein sequence with binding affinity to cell receptors and integrins, the sequences are found in plasma proteins such a fibrinogen, fibronectin and vitronectin) coupled adjacent to the fluorine tails of the BFSM such that the [Bio] component can provide specific binding affinity and function to select cells migrating on the biomaterial surface. In addition, this BFSM can contribute to enhancing the biocompatible nature of the polymer surface, in which the BFSM is added to, with the interfacing biological environment, specifically controlling and permitting the integration of cells with an implant and more specifically tissue engineering implant devices. LDI/PTMO/I/GGRGD is synthesized with lysine diisocyanate as both the linkA and linkB reactants, polytetramethylene oxide diol (molecular weight of 1000) (PTMO) was used as the oligo component, fraction (I) of the fluoroalcohol BA-L was used as the fluoro component and glycine-glycine-arginine-glycine-aspartic acid peptide is the [Bio] component use as a representative oligopeptide fragment (<20 amino-acids) related to plasma and other proteins which interact in specific ways with cells. This BFSM will be referred to as LDI/PTMO/I/GGRGD, throughout this text. The conditions of synthesis for this reaction are as follows.

10 grams of PTMO are reacted with 4.1 grams of LDI for two hours and then 11.7 grams (25% excess) of "I" were added to the reaction. The mixture is reacted in a nitrogen atmosphere with 50 mg of the catalyst, dibutyltin dilaurate, in 100 mLs of dimethylacetamide (DMAc) and the reaction temperature was maintained between 60–70° C. for 2.5 hours. The product of the latter reaction is precipitated in a mixture of distilled water with ether to remove residual fluoro reactant. The product of this step is dried under vacuum at 60° C. Activation of the methyl ester on [linkB] is carried out by hydrolysis of the protective ester group by dissolving the BFSM precursor in dimethylformamide (DMF) and adjusting the acid content in the DMF solution, using an aqueous 1.0 N hydrochloric acid solution, to a pH reading of 1.5 on a pH meter. The solution temperature is then raised to 45° C. for 4 hours. The acidified BFSM precursor is then precipitated in 1 M aqueous KCl, washed in distilled water and dried under vacuum at 60° C. for 48 hours. The acid group of the acidified BFSM precursor is then reacted with oxalyl chloride in a nitrogen atmosphere to introduce a chloride leaving group on the acid. The solution is first cooled to 5° C. with an ice bath and oxalyl chloride is added stoichiometrically to the amount of acid groups to scavenge free HCl which is generated as a by-product. The latter reaction step produces an acid chloride BFSM precursor which is then reacted with the amine terminal of the GGRGD (SEQ ID NO: 5) peptide sequence (peptide side chains were protected to eliminate cross-reactions with the arginine and carboxylic acid side groups; peptide is supplied from the analytical laboratories at the Hospital for Sick Children, Toronto). GGRGD (SEQ ID NO: 5) peptide was dispersed in pyridine and added to the acid chloride BESM precursor reaction mixture and the solution is allowed to react overnight at 20° C. The final BFSM is precipitated in a mixture of methanol/1M aqueous KCl solution (30/70 vol %). The precipitated polymer is then washed three times in distilled water. Following washing the material is dried under vacuum. The fluorine wt % fluorine is anticipated to yield a value of approximately 10%, depending on the exact distribution of oligomers and the efficiency of product recovery. This fluorine content is above the typical cut-off value of 1% at which point selective migration of BFMS to the surface becomes compromised by competing dispersion and dipole-dipole interactions of the BESM with the base polymer substrate. The theoretical molecular weight based on stoichiometry is approximately $4.0\times10^3$.

EXAMPLE 6

LDI/PTMO/I/GGRGD-2 is identical to the BFSM in Example 5 with the exception that rather than coupling the GGRGD (SEQ ID NO: 5) sequence with oxalyl chloride, an alternate leaving group was generated by using the EDC/NHS method described in example 2. All reaction conditions were identical to that of Example 5 up to the formation of the acidified precursor BESM. Activation of the methyl ester on [linkB] is carried out by hydrolysis of the protective ester group by dissolving the BESM precursor in methanol (MeOH) and adding 1N NaOH in the MeOH solution, to a stoichiometric ratio 5% excess relative to the ester groups. The solution temperature was maintained at 20° C. for 18 hours. A 10% excess of 1 N HCl solution (relative to the amount of base added in the previous step) was added and stirred for 1 hour. The acidified BESM precursor was then precipitated distilled water, washed and dried under vacuum at 60° C. for 24 hours. The acid group of the acidified BFSM precursor was then reacted with 1-ethyl-3-(3-dimethylamino-propyl carbodiimide (EDC) (in a 3:1 molar ratio of EDC:acid groups) and N-hydroxysuccinimide (NHS) (in a 1:1 molar ratio with EDC) in a nitrogen atmosphere to introduce a succinimide group on the acid. This solution reacts in DMF for 3 hours at 20° C. and the pH is maintained at 5.5. The latter reaction step produces a succinimide BFSM precursor which is then reacted with the terminal amine of the GGRGD (SEQ ID NO: 5) peptide. GGRGD (SEQ ID NO: 5) peptide is dispersed in pyridine and added to the succinimide BFSM precursor reaction mixture and the solution is allowed to react overnight at 20° C. The final BFSM is precipitated in a mixture of methanol/1M aqueous KCl solution (30/70 vol %). The precipitated polymer is then washed three times in distilled water. Following washing the material is dried under vacuum. The fluorine wt % fluorine is anticipated to yield a value of approximately 10%, depending on the exact distribution of oligomers and the efficiency of product recovery. This fluorine content is above the typical cut-off value of 1% at which point selective migration of BFSM to the surface becomes compromised by competing dispersion and dipole-dipole interactions of the BESM with the base polymer substrate. The theoretical molecular weight based on stoichiometry is approximately $4.0 \times 10^3$.

EXAMPLE 7

HDI-DABS/PTMO/I/NORF is an example of a BFSM with a stoichiometry that introduces a fluorine content of approximately 10 wt % and pendent Norfloxacin moieties. HDI-DABS/PTMO/I/NORF differs from LDI/PCN/I/NORF in Example 3 in that it is synthesized with a different linkB molecule and used PTMO rather than PCN as the oligo molecule. LinkB is synthesized with diamino benzene sulfonic acid which is reacted with HDI to produce a new diisocyanate linking molecule, to be used as both the linkA and linkB reactants. The latter is reacted with polytetramethylene oxide diol (molecular weight of 1000) (PTMO). Hence, PTMO was used as the oligo component, fraction (I) of the fluoroalcohol BA-L was used as the fluoro component and Norfloxacin was the [Bio] component. This BFSM will be referred to HDI-DABS/PTMO/I/NORF, throughout this text. The conditions of synthesis for this reaction are as follows.

10 grams of PTMO are reacted with 9.2 grams of HDI-DABS for two hours and then 11.7 grams (25% excess) of "I" are added to the reaction. The mixture is reacted in a nitrogen atmosphere with 50 mg of the catalyst, dibutyltin dilaurate, in 100 mLs of dimethylacetamide (DMAc) and the reaction temperature was maintained between 60–70° C. for 2.5 hours. The product of the latter reaction is precipitated in a mixture of distilled water with ether to remove residual [fluoro] reactant. The product of this step is dried under vacuum at 60° C. Activation of the sulfonic acid on linkB is carried out by a reaction with oxalyl chloride in a nitrogen atmosphere to introduce a chloride leaving group on the acid. The solution is first cooled to 5° C. with an ice bath and oxalyl chloride is added stoichiometrically to the amount of acid groups. Triethylamine is added stoichiometrically to the amount of acid groups to scavenge free HCl which is generated as a by-product. The latter reaction step produces a sulfonyl chloride BFSM precursor which is then reacted with the secondary amine of the norfloxacin molecule. Norfloxacin is dissolved in DMF and added to the sulfonyl chloride BFSM precursor reaction mixture and the solution is allowed to react overnight at 20° C. The final BFSM is precipitated in a mixture of ethanol/1M aqueous KCl solution (30/70 vol %). The precipitated polymer is then washed three times in an 80/20 vol % ethanol/water mixture. Following washing the material is dried under vacuum. The fluorine wt % fluorine is anticipated to yield a value of approximately 10%, depending on the exact distribution of oligomers and the efficiency of product recovery. This fluorine content is above the typical cut-off value of 1% at which point selective migration of BFMS to the surface becomes compromised by competing dispersion and dipole-dipole interactions of the BFSM with the base polymer substrate. The theoretical molecular weight based on stoichiometry is approximately $3.6 \times 10^3$.

EXAMPLE 8

LDI/PDMS/I/NORF is an example of a BFSM with a stoichiometry that introduces a fluorine content of approximately 3.2 wt % and pendent Norfloxacin moieties. LDI/PDMS/I/NORF differs from Example 3 in that it contains a siloxane oligo component rather than a carbonate oligo component, in order to-optimize the BFSMs compatibility with silicone based substrates. As well, it shows the reaction of a diamino oligo component rather than a diol. LDI/PDMS/I/NORF is synthesized with lysine diisocyanate as both the linkA and linkB reactants. Polydimethylsiloxane-bis (3-aminopropyl) terminated (PDMS) was use as the oligo component, fraction (I) of the fluoroalcohol BA-L was used as the fluoro reactant and Norfloxacin is the [Bio] component. This BFSM is referred to LDI/PDMS/I/NORF, throughout this text. The conditions of synthesis for this reaction are as follows.

25.1 grams of PDMS are reacted with 4.2 grams of LDI for two hours and then 14.2 grams (50% excess) of "I" are added to the reaction. The mixture is reacted in a nitrogen atmosphere with 60 mg of the catalyst, dibutyltin dilaurate, in 100 mLs of tetrahydrofuran. The reaction temperature for LDI with PDMS is 15° C. and for the coupling of "I" its starts at 20 and finishes at 50° C. The product of the latter reaction is precipitated in a mixture of distilled water with ether to remove residual fluoro reactant, and washed in a MeOH/water mixture of 30/70. The product of this step is dried under vacuum at 60° C. overnight. Activation of the methyl ester on [linkB] is carried out by hydrolysis of the protective ester group by dissolving the BFSM precursor in acetone and then adding MeOH to yield a 50/50 mixture of the two solvents. 1N NaOH was added to the acetone/MeOH solution, to a stoichiometric ratio +5% excess relative to the ester groups. The solution temperature was maintained at 20° C. for 18 hours. A 10% excess of 1 N HCl solution (relative to the amount of base added in the previous step) was added and stirred for 1 hour. The acidified BFSM precursor was then precipitated distilled water, washed and dried under vacuum at 60° C. for 24 hours. The acid group of the acidified BFSM precursor is then dissolved in diclo-romethane and reacted with oxalyl chloride in a nitrogen atmosphere to introduce a chloride leaving group on the acid. The solution is first cooled to 5° C. with an ice bath and oxalyl chloride is added stoichiometrically to the amount of acid groups. The latter reaction step produces an acid chloride BFSM precursor which is then reacted with the secondary amine of the norfloxacin molecule. Norfloxacin is dissolved in pyridine and added to the acid chloride BFSM precursor reaction mixture and the solution is allowed to react overnight at 20° C. The pyridine also acts as an acid scavenger for residual HCl generated in the previous step. The final BFSM is precipitated upon cooling the reaction mixture to 15° C. and subsequent washing in water. Residual drug is separated by redissolving the polymer in THF and then recovering the non-soluble drug by centrifuging and decanting the polymer solution. The polymer is then recovered by cooling and washing in water. Following washing the material is dried under vacuum. The fluorine wt % fluorine is approximately 3.2%, depending on the exact distribution of oligomers and the efficiency of product recovery. This fluorine content is above the typical cut-off value of 1% at which point selective migration of BFMS to the surface becomes compromised by competing dispersion and dipole-dipole interactions of the BFSM with the base polymer substrate. The theoretical molecular weight based on stoichiometry is approximately $8 \times 10^3$.

EXAMPLE 9

LDI/THDI-DPS/I/NORF is an example of a BFSM with a stoichiometry that introduces a fluorine content of approximately 12 wt % and pendent Norfloxacin moieties. LDI/ THDI-DPS/I/NORF differs from Example 3 in that is contains a poly[urethane/sulfone] oligo component rather than a carbonate oligo component. This was selected in order to optimize the BFSM's compatibility with polyethersulfone based substrates. LDI/THDI-DPS/I/NORF is synthesized with trimethyl- 1,6 diisocyanatohexane (THDI) as a LinkA reactant and lysine diisocyanate as a linkB reactant, THDI combines with dihydroxy diphenylsulfone (DPS) to make the urethane/sulfone oligo component, fraction (I) of the fluoroalcohol BA-L was used as the fluoro reactant and Norfloxacin is the [Bio] component. This BFSM is referred to as LDI/THDI-DPS/I/NORF, throughout this text. The conditions of synthesis for this reaction are as follows.

23 grams of THDI-DPS with terminal hydroxyls (4:5 molar ratio respectively) are reacted with 8.5 grams of LDI for 2.5 hours and then 25 grams (50% excess) of "I" are added to the reaction. The mixture is reacted in a nitrogen atmosphere with 50 mg of the catalyst, dibutyltin dilaurate, in 120 mLs of DMAc and the reaction temperature was maintained at 60° C. The product of the latter reaction is precipitated in a mixture of distilled water with ether to remove residual [fluoro] compounds. The product of this step is dried under vacuum at 60° C. Activation of the methyl ester on [linkB] is carried out by hydrolysis of the protective ester group by dissolving the BFSM precursor in methanol (MeOH) and adding 1N NaOH in the MeOH solution, to a stoichiometric ratio +5% excess relative to the ester groups. The solution temperature was maintained at 20° C. for 18 hours. A 10% excess of 1 N HCl solution (relative to the amount of base added in the previous step) was added and stirred for 1 hour. The acidified BFSM precursor was then precipitated distilled water, washed and dried under vacuum at 60° C. for 24 hours. The acid group of the acidified BFSM precursor is then reacted with oxalyl chloride in a nitrogen atmosphere to introduce a chloride leaving group on the acid. A solution of acidified BFSM in DMF is first cooled to 5° C. with an ice bath and oxalyl chloride is added stoichiometrically to the amount of acid groups. The latter reaction step produces an acid chloride BFSM precursor which is then reacted with the secondary amine of the norfloxacin molecule. Norfloxacin is dissolved in pyridine and added to the acid chloride BFSM precursor reaction mixture and the solution is allowed to react overnight at 20° C. The pyridine also acts as an acid scavenger for residual HCl generated in the previous step. The final BFSM is precipitated in a mixture of ethanol/1M aqueous KCl solution (30/70 vol %). The precipitated polymer is then washed three times in an 80/20 vol % ethanol/water mixture. Following washing the material is dried under vacuum. The fluorine wt % fluorine is approximately 12%, depending on the exact distribution of oligomers and the efficiency of product recovery. This fluorine content is above the typical cut-off value of 1% at which point selective migration of BFMS to the surface becomes compromised by competing dispersion and dipole-dipole interactions of the BFSM with the base polymer substrate. The theoretical molecular weight based on stoichiometry is approximately $4.5 \times 10^3$.

EXAMPLE 10

LDI/PEB/I/NORF is an example of a BFSM with a stoichiometry that introduces a fluorine content of 8 wt % and pendent Norfloxacin moieties. LDI/PEB/I/NORF differs from LDI/PCN/I/NORF in Example 3 in the nature of the oligo segment. Polyethylene-butylene co-polymer diol (PEB) was selected in order to optimize the BFSM's compatibility with a polypropylene based substrate. LDI/PEB/ H/NORF was synthesized with lysine diisocyanate as both the linkA and linkB reactants, PEB (molecular weight of 2500) was used as the oligo component, fraction (I) of the fluoroalcohol BA-L was used as the fluoro reactant and Norfloxacin was used as the [Bio] component. This BFSM is referred to as LDI/PEB/I/NORF, throughout this text. The conditions of synthesis for this reaction are as follows.

25 grams of PEB are reacted with 4.2 grams of LDI for two hours and then 13 grams (50% excess) of "I" were added to the reaction. The mixture was reacted in a nitrogen atmosphere with 100 mg of the catalyst, dibutyltin dilaurate, in 200 mLs of toluene and the reaction temperature was maintained between 60–70° C. overnight. The product of the latter reaction is precipitated in ether to remove residual [fluoro] compounds and washed in MeOH. The product of this step is dried under vacuum at 60° C. Activation of the methyl ester on [linkB] is carried out by hydrolysis of the protective ester group by dissolving the BFSM precursor in toluene with the addition of methanol (in a 4:1 molar ratio of toluene:MeOH), and adding 1N NaOH, to a stoichiometric ratio +5% excess relative to the ester groups. The solution temperature was maintained at 20° C. for 18 hours. A 10% excess of 1 N HCl solution (relative to the amount of base added in the previous step) was added and stirred for 1 hour. The acidified BFSM precursor was then precipitated distilled water, washed and dried under vacuum at 60° C. for 24 hours. The acid group of the acidified BFSM precursor is then reacted with oxalyl chloride in a nitrogen atmosphere to introduce a chloride leaving group on the acid. A solution of acidified BFSM in toluene is first cooled to 5° C. with an ice bath and oxalyl chloride is added stoichiometrically to the amount of acid groups. The latter reaction step produces an acid chloride BFSM precursor which is then reacted with the secondary amine of the norfloxacin molecule. Norfloxacin is dissolved in pyridine and added to the acid chloride BFSM precursor reaction mixture and the solution is allowed to react overnight at 20° C. The pyridine also acts as an acid scavenger for residual HCl generated in the previous step. The final BFSM is precipitated in a mixture of methanol/1M aqueous KCl solution (30/70 vol %). Following washing in distilled water, the material is dried under vacuum. The fluorine wt % fluorine is approximately 8%, depending on the exact distribution of oligomers and the efficiency of product recovery. This fluorine content is above the typical cut-off value of 1% at which point selective migration of BFSM to the surface becomes compromised by competing dispersion and dipole-dipole interactions of the BFSM with the base polymer substrate. The theoretical molecular weight based on stoichiometry is approximately $5.0 \times 10^3$.

EXAMPLE 11

LDI/PCN/I/HYA is an example of a BFSM with a stoichiometry that introduces a fluorine content of 5 wt % and pendent oligo-hyaluronic acid (HYA) (approximate molecular weight 3000, procured from Genzyme, Mass.) molecules coupled adjacent to the fluorine tails of the BFSM such that the molecule can promote the adhesion of new tissue structures and the related cells for formation of new biological tissues. LDI/PCN/I/HYA was synthesized with lysine diisocyanate as both the linkA and linkB reactants. Polycarbonate diol (molecular weight of 970) (PCN) was used as the oligo component, fraction (I) of the fluoroalcohol BA-L was used as the fluoro reactant and oligo-hyaluronic acid was used as the [Bio] component. This BFSM is referred to as LDI/PCN/I/HYA, throughout this text. The conditions of synthesis for this reaction are as follows.

5 grams of PCN are reacted with 2 grams of LDI for two hours and then 3.2 grams of "I" were added to the reaction.

The mixture was reacted in a nitrogen atmosphere with 2 mg of the catalyst, dibutyltin dilaurate, in 65 mLs of dimethylacetamide (DMAc) and the reaction temperature was maintained between 60–70° C. for 2.5 hours. The product of the latter reaction is precipitated in a mixture of distilled water with ether to remove residual [fluoro] compounds. The product of this step is dried under vacuum at 60° C. Activation of the methyl ester on [linkB] is carried out by hydrolysis of the protective ester group by dissolving the BFSM precursor in dimethylformamide (DMF) and adjusting the acid content in the DMF solution, using an aqueous 1.0 N hydrochloric acid solution, to a pH reading of 1.5 on a pH meter. The solution temperature is then raised to 45° C. for 4 hours. The acidified BFSM precursor is then precipitated in 1 M aqueous KCl, washed in distilled water and dried under vacuum at 60° C. for 48 hours. The acidified BFSM precursor was then precipitated distilled water, washed and dried under vacuum at 60° C. for 24 hours. The acid group of the acidified BFSM precursor was then reacted with 1-ethyl-3-(3-dimethylamino-propyl carbodiimide (EDC) (in a 3:1 molar ratio of EDC:acid groups) and N-hydroxysuccinimide (NHS) (in a 1:1 molar ratio with EDC) in a nitrogen atmosphere to introduce a succinimide group on the acid. This solution reacts in DMF for 3 hours at 20° C. and the pH is maintained at 5.5. The latter reaction step produces a succinimide BFSM precursor which is then reacted with the hydroxyl of the hyaluronic acid molecule. Hyaluronic acid is dissolved in 0.2 wt % aqueous NaCl solution and added to the succinimide BFSM precursor reaction mixture and the solution was allowed to react for 24 hrs at 20° C. The final BFSM is precipitated in a mixture of methanol/1M aqueous KCl solution (30/70 vol %). The precipitated polymer was then washed three times in distilled water. Following washing the material is dried under vacuum. The fluorine wt % fluorine is anticipated to yield a fluorine content of approximately 5%, depending on the exact distribution of oligomers and the efficiency of product recovery. This fluorine content is above the typical cut-off value of 1% at which point selective migration of BFSM to the surface becomes compromised by competing dispersion and dipole-dipole interactions of the BFSM with the base polymer substrate. The theoretical molecular weight based on stoichiometry is approximately $8.5 \times 10^3$.

EXAMPLE 12

LDI/HDI-PTMO-PPO/I/HEP is an example of a BFSM with a stoichiometry that introduces a fluorine content of 4.6 wt % and pendent Heparin molecules coupled adjacent to the fluorine tails of the BFSM such that the molecule can catalyse the deactivation of thrombin (in key protein involved in the upregulation of clot formation) via antithrombin III (a key inhibitor of the clot forming process) at the surface of the polymer. In addition, this BFSM can contribute to enhancing the biocompatible nature of the polymer surface, in which the BFSM is added, with the interfacing biological environment, specifically reducing the potential for blood to form uncontrolled thrombus growth on a biomaterial surface and generate subsequent embolization events. LDI/HDI-PTMO-PPO/I/HEP differs from LDI/PTMO/I/HEP in Example 2 in the nature of the oligo segment. This was selected in order to demonstrate the ability to tailor the BFSM's compatibility with polyetherurethane based substrates. LDI/HDI-PTMO-PPO/I/HEP is synthesized with 1,6 diisocyanatohexane (HDI) as a LinkA reactant and lysine diisocyanate as a linkB reactant, HDI combines with polytetramethylene oxide (approximate molecular weight 500) and polypropylene oxide (approximate molecular weight 425 PPO) to make the urethane/ether oligo component, fraction (I) of the fluoroalcohol BA-L was used as the fluoro component and Heparin sulfate was used as the [Bio] component. This BFSM is referred to as LDI/HDI-PTMO-PPO/I/HEP, throughout this text. The conditions of synthesis for this reaction are as follows.

9.7 grams of HDI-PTMO-PPO with terminal hydroxyls (1:1:1 molar ratio respectively) are reacted with 1.9 grams of LDI for two hours and then 11 grams of "I" were added to the reaction. The mixture was reacted in a nitrogen atmosphere with 50 mg of the catalyst, dibutyltin dilaurate, in 100 mLs of dimethylacetamide (DMAc) and the reaction temperature was maintained between 60–70° C. The product of the latter reaction is precipitated in a mixture of distilled water with ether to remove residual fluoro reactant. The product of this step is dried under vacuum at 60° C. Activation of the methyl ester on [linkB] is carried out by hydrolysis of the protective ester group by dissolving the BFSM precursor in methanol (MeOH) and adding 1N NaOH in the MeOH solution, to a stoichiometric ratio +5% excess relative to the ester groups. The solution temperature was maintained at 20° C. for 18 hours. A 10% excess of 1 N HCl solution (relative to the amount of base added in the previous step) was added and stirred for 1 hour. The acidified BFSM precursor was then precipitated distilled water, washed and dried under vacuum at 60° C. for 24 hours. The acid group of the acidified BFSM precursor was then reacted with 1-ethyl-3-(3-dimethylamino-propyl carbodiimide (EDC) (in a 3:1 molar ratio of EDC:acid groups) and N-hydroxysuccinimide (NHS) (in a 1:1 molar ratio with EDC) in a nitrogen atmosphere to introduce a succinimide group on the acid. This solution reacts in DMF for 3 hours at 20° C. and the pH is maintained at 5.5. The latter reaction step produces a succinimide BFSM precursor which is then reacted with the hydroxyl or amines of the heparin molecule. Heparin was dissolved in 0.2 wt % aqueous NaCl solution and added to the succinimide BFSM precursor reaction mixture and the solution was allowed to react for 24 hrs at 20° C. The final BFSM is precipitated in a mixture of methanol/1M aqueous KCl solution (30/70 vol %). The precipitated polymer was then washed three times in distilled water. Following washing the material is dried under vacuum. The fluorine wt % fluorine is anticipated to yield a fluorine content of approximately 5%, depending on the exact distribution of oligomers and the efficiency of product recovery. This fluorine content is above the typical cut-off value of 1% at which point selective migration of BFSM to the surface becomes compromised by competing dispersion and dipole-dipole interactions of the BFSM with the base polymer substrate. The theoretical molecular weight based on stoichiometry is approximately $8.5 \times 10^3$.

EXAMPLE 13

LDI/PTMO/I/HC is an example of a BFSM which contains a high fluorine content and a pendent hydrocortisone molecule coupled adjacent to the fluorine tails of the BFSM such that the molecule can reduce the inflammation associated white blood cell activation. In addition this BFSM can contribute to enhancing the biocompatible nature of the polymer surface, in which the BFSM is added to, with the interfacing biological environment, specifically reducing the extent of macrophage activation by the biomaterial surface. LDI/PTMO/I/HC was synthesized with lysine diisocyanate as both the linkA and linkB reactants. Polytramethylene oxide diol (molecular weight of 1000) (PTMO) was use as the oligo component. Fraction (I) of the fluoroalcohol BA-L was used as the fluoro reactant and hydrocortisone was used as the [Bio] component. This BFSM is referred to as LDI/PTMO/I/HC, throughout this text. The conditions of synthesis for this reaction are as follows.

10 grams of PTMO were reacted with 4.1 grams of LDI for two hours and then 11 grams of "I" were added to the reaction. The mixture was reacted in a nitrogen atmosphere with 50 mg of the catalyst, dibutyltin dilaurate, in 100 mLs of dimethylacetamide (DMAc) and the reaction temperature was maintained between 60–70° C. for 2.5 hours. The product of the latter reaction is precipitated in a mixture of distilled water with ether to remove residual fluoro reactant. The product of this step is dried under vacuum at 60° C. Activation of the methyl ester on [linkB] is carried out by hydrolysis of the protective ester group by dissolving the BFSM precursor in methanol (MeOH) and adding 1N NaOH in the MeOH solution, to a stoichiometric ratio +5% excess relative to the ester groups. The solution temperature was maintained at 20° C. for 18 hours. A 10% excess of 1 N HCl solution (relative to the amount of base added in the previous step) was added and stirred for 1 hour. The acidified BFSM precursor was then precipitated distilled water, washed and dried under vacuum at 60° C. for 24 hours. The acid group of the acidified BFSM precursor was then reacted with 1-ethyl-3-(3-dimethylamino-propyl carbodiimide (EDC) (in a 3:1 molar ratio of EDC:acid groups) and N-hydroxysuccinimide (NHS) (in a 1:1 molar ratio with EDC) in a nitrogen atmosphere to introduce a succinimide group on the acid. This solution reacts in DMF for 3 hours at 20° C. and the pH is maintained at 5.5. The latter reaction step produces a succinimide BFSM precursor which is then reacted with the hydroxyl on the hydrocortisone molecule. Hydrocortisone was dissolved in DMF and added to the succinimide BFSM precursor reaction mixture and the solution is allowed to react overnight at 20° C. The final BFSM was precipitated in 1M aqueous KCl solution. The precipitated polymer was then washed three times in distilled water. Following washing the material is dried under vacuum. The wt % fluorine is anticipated to yield a value of approximately 12%, depending on the exact distribution of oligomers and the efficiency of product recovery. This fluorine content is above the typical cut-off value of 1% at which point selective migration of BFSM to the surface becomes compromised by competing dispersion and dipole-dipole interactions of the BFSM with the base polymer substrate. The polydispersity is 1.3. The theoretical molecular weight based on stoichiometry is approximately $3.0 \times 10^3$.

EXAMPLE 14

LDI/PTMO/I/GPC is an example of a BFSM which contains a high fluorine content and a pendent phospholipid molecule (L-α-glycerophosphorycholine) coupled adjacent to the fluorine tails of the BFSM such that the molecule can control cell/cell phospholipid membranes interactions to reduce blood cell activation. In addition, this BFSM can contribute to specifically reducing platelet activation which leads to thrombus formation on medical device surfaces. LDI/PTMO/I/GPC was synthesized with lysine diisocyanate (used as both the [linkA] and [linkB] components), polytramethylene oxide diol (molecular weight of 1000) (PTMO) was use as the [oligo] component, fraction (I) of the fluoroalcohol BA-L was used as the [fluoro] component and L-α-glycerophosphorycholine was used as the [Bio] component. This BFSM will be referred to LDI/PTMO/I/GPC, throughout this text. The conditions of synthesis for this reaction are as follows. 10 grams of PTMO were reacted with 4.1 grams of LDI for two hours and then 11 grams of "I" were added to the reaction. The mixture was reacted in a nitrogen atmosphere with 50 mg of the catalyst, dibutyltin dilaurate, in 100 mLs of dimethylacetamide (DMAc) and the reaction temperature was maintained between 60–70° C. for 2.5 hours. The product of the latter reaction is precipitated in a mixture of distilled water with ether to remove residual [fluoro] compounds. The product of this step is dried under vacuum at 60° C. Activation of the methyl ester on [linkB] is carried out by hydrolysis of the protective ester group by dissolving the BFSM precursor in methanol (MeOH) and adding 1N NaOH in the MeOH solution, to a stoichiometric ratio +5% excess relative to the ester groups. The solution temperature was maintained at 20° C. for 18 hours. A 10% excess of 1 N HCl solution (relative to the amount of base added in the previous step) was added and stirred for 1 hour. The acidified BFSM precursor was then precipitated distilled water, washed and dried under vacuum at 60° C. for 24 hours. The acid group of the acidified BFSM precursor was then reacted with 1-ethyl-3-(3-dimethylamino-propyl carbodiimide (EDC) (in a 3:1 molar ratio of EDC:acid groups) and N-hydroxysuccinimide (NHS) (in a 1:1 molar ratio with EDC) in a nitrogen atmosphere to introduce a succinimide group on the acid. This solution reacts in DMF for 3 hours at 20° C. and the pH is maintained at 5.5. The latter reaction step produces a succinimide BFSM precursor which is then reacted with the terminal hydroxyl on the L-α-Glycerophosphorycholine molecule. L-α-Glycerophosphorycholine is dissolved in pyridine and added to the succinimide BFSM precursor reaction mixture and the solution is allowed to react overnight at 20° C. The final BFSM is precipitated in 1M aqueous KCl solution. The precipitated polymer is then washed three times in distilled water. Following washing the material is dried under vacuum. The wt % fluorine is anticipated to yield a value of approximately 12%, depending on the exact distribution of oligomers and the efficiency of product recovery. This fluorine content is above the typical cut-off value of 1% at which point selective migration of BFSM to the surface becomes compromised by competing dispersion and dipole-dipole interactions of the BFSM with the base polymer substrate. The polydispersity is 1.3. The theoretical molecular weight based on stoichiometry is approximately $3.0 \times 10^3$.

EXAMPLE 15

LDI/PHE/I/HYA is an example of a BFSM with a stoichiometry that introduces a fluorine content of 3 wt % and pendent oligo-hyaluronic acid (HYA) (approximate molecular weight 3000, procured from procured from Genzyme, Mass.) moieties coupled adjacent to the fluorine tails of the BFSM such that the molecule can promote the adhesion of new tissue structures and the related cells for formation of new biological tissues. This BFSM differs from that of example 13 in that it is synthesized with an oligo-amide segment rather than an oligo-carbonate segment. LDI/PHE/I/HYA is synthesized with lysine diisocyanate as both the linkA and linkB reactants. Oligo-phenyl alanine with terminal amines (molecular weight of 5–15kD) (PHE) is used as the oligo component, while fraction (I) of the fluoroalcohol BA-L is used as the fluoro component and oligo-hyaluronic acid is used as the [Bio] component. This BFSM is referred to as LDI/PHE/I/HYA, throughout this text. The conditions of synthesis for this reaction are as follows.

50 grams of PHE are reacted with 2 grams of LDI for two hours and then 3.2 grams of "I" were added to the reaction. The mixture was reacted in a nitrogen atmosphere with 2 mg of the catalyst, dibutyltin dilaurate, in 400 mLs of dimethylacetamide (DMAc) and the reaction temperature was maintained between 60–70° C. for 2.5 hours. The product of the latter reaction is precipitated in a mixture of distilled water with ether to remove residual [fluoro] compounds. The product of this step is dried under vacuum at 60° C. Activation of the methyl ester on [linkB] is carried out by mild hydrolysis of the protective ester group by dissolving the BFSM precursor in dimethylformamide (DMF) and adjusting the acid content in the DMF solution, using an aqueous 1.0 N hydrochloric acid solution, to a pH reading of 1.5 on a pH meter. The solution temperature is then raised to 45° C. for 4 hours. The acidified BFSM precursor is then precipitated in 1 M aqueous KCl, washed in distilled water and dried under vacuum at 60° C. for 48 hours. The acidified BFSM precursor was then precipitated distilled water, washed and dried under vacuum at 60° C. for 24 hours. The acid group of the acidified BFSM precursor was then reacted with 1-ethyl-3-(3-dimethylamino-propyl carbodiimide (EDC) (in a 3:1 molar ratio of EDC:acid groups) and N-hydroxysuccinimide (NHS) (in a 1:1 molar ratio with EDC) in a nitrogen atmosphere to introduce a succinimide group on the acid. This solution reacts in DMF for 3 hours at 20° C. and the pH is maintained at 5.5. The latter reaction step produces a succinimide BFSM precursor which is then reacted with the hydroxyl of the hyaluronic acid molecule. Hyaluronic acid is dissolved in 0.2 wt % aqueous NaCl solution and added to the succinimide BFSM precursor reaction mixture and the solution was allowed to react for 24 hrs at 20° C. The final BFSM is precipitated in a mixture of methanol/1M aqueous KCl solution (30/70 vol %). The precipitated polymer was then washed three times in distilled water. Following washing the material is dried under vacuum. The 30 fluorine wt % fluorine is anticipated to yield a fluorine content of approximately 3%, depending on the exact distribution of oligomers and the efficiency of product recovery. This fluorine content is above the typical cut-off value of 1% at which point selective migration of BFSM to the surface becomes compromised by competing dispersion and dipole-dipole interactions of the BFSM with the base polymer substrate. The theoretical molecular weight based on stoichiometry is approximately $1.5 \times 10^4$.

EXAMPLE 16

LDI/PTMO/I/GHG is an example of a BFSM with a stoichiometry that introduces a fluorine content of 4.5 wt % and pendent oligonucleotide GHG (genetics housekeeping probe, TAT GAG TCT ACC CAC GGC AAG TTC AA-OH-5' (SEQ ID NO: 6), approximate molecular weight of 7800) coupled adjacent to the fluorine tails of the BFSM to demonstrate the ability of binding DNA recognition probes for potential applications in bio-diagnostics. This particular DNA sequence is known as a house keeping gene and is expressed in all cells to provide basic function needed for cell survival. LDI/PTMO/I/GHG was synthesized with lysine diisocyanate as both the linkA and linkB reactants. Polytetramethylene oxide diol (molecular weight of 1000) (PTMO) was use as the oligo component, the fraction (I) of the fluoroalcohol BA-L as the fluoro reactant, and base pair of GHG (5'-pATA CTG AGA TGG GTG CCG TTC TAT GAC TCT ACC

CAC GGC AAG TTC AA-OH-5' (SEQ ID NO: 1).

The latter was used as the starting material because it contains the match base pairs for GHG and protects the DNA sequence during the coupling reaction to the BFSM. This BFSM is referred to as LDI/PTMO/I/GHG, throughout this text. The conditions of synthesis for this reaction are as follows.

10 grams of PTMO are reacted with 4.1 grams of LDI for two hours and then 11.7 grams (25% stoichiometric excess) of "I" were added to the reaction. The mixture was reacted in a nitrogen atmosphere with 50 mg of the catalyst, dibutyltin dilaurate, in 100 mLs of dimethylacetamide (DMAc) and the reaction temperature was maintained between 60–70° C. for 2.5 hours. The product of the latter reaction is precipitated in a mixture of distilled water with ether to remove residual fluoro reactant. The product of this step is dried under vacuum at 60° C. Activation of the methyl ester on [linkB] is carried out by hydrolysis of the protective ester group by dissolving the BFSM precursor in methanol (MeOH) and adding 1N NaOH in the MeOH solution, to a stoichiometric ratio +5% excess relative to the ester groups. The solution temperature was maintained at 20° C. for 18 hours. A 10% excess of 1 N HCl solution (relative to the amount of base added in the previous step) was added and stirred for 1 hour. The acidified BFSM precursor was then precipitated distilled water, washed and dried under vacuum at 60° C. for 24 hours. Then 50% of the acid groups in the acidified BFSM precursor were reacted with 1-ethyl-3-(3-dimethylamino-propyl carbodiimide (EDC) (in a 3:1 molar ratio of EDC:acid groups) and N-hydroxysuccinimide (NHS) (in a 1:1 molar ratio with EDC) in a nitrogen atmosphere to introduce a succinimide group on the acid. This solution reacts in DMF for 3 hours at 20° C. and the pH is maintained at 5.5. The latter reaction step produces a succinimide BFSM precursor which is then reacted with the 5' hydroxyl terminal of the GHG base pair. The GHG base pair was dissolved in 0.2 wt % aqueous PBS buffer, pH 6.0 solution and added to the succinimide BFSM precursor reaction mixture and the solution was allowed to react for 24 hrs at 20° C. The pH of the reaction mixture is then adjusted to a pH of 7.5 in order ligate the protective base pair from the BFSM. The final BFSM is precipitated in a mixture of methanol/1M aqueous KCl solution (30/70 vol %). The precipitated polymer is then washed three times in distilled water. Following washing the material is dried under vacuum. The fluorine wt % fluorine is anticipated to yield a fluorine content of approximately 4.5%, depending on the exact distribution of oligomers and the efficiency of product recovery. This fluorine content is above the typical cut-off value of 1% at which point selective migration of BFSM to the surface becomes compromised by competing dispersion and dipole-dipole interactions of the BFSM with the base polymer substrate. The theoretical molecular weight based on stoichiometry is approximately $10.5 \times 10^3$.

EXAMPLE 17

Upon reaction of 5 wt % LDI/PCN/I/VITE (Example 1) with HDI/PCN/BD, a polycarbonate based polyurethane synthesized from 1,6 hexamethylene diisocyanate, polycarbonate diol (molecular weight 970, butane diol and dibutyltin dilaurate catalyst (Aldrich Chemical Company), it was observed that the additive migrated to the surface. Evidence of this is provided by X-ray photoelectron which showed the surface atomic fluorine content within the top 10 nm increased from background levels (<2 atomic weight %) to (>than 40 atomic weight %). This increase in fluorine content implies that more than 60% of the atoms on the surface are associated with the fluorocarbon tails of the BFSM molecules. It also suggests that the fluorine and its immediately adjacent segments within the BFSM occupy a dominant component of the upper surface. The changes in surface chemistry are further observed from contact angle data, specifically advancing contact angle data, which is a measure of a the surface's hydrophobic components. This shows significant increases from 70.6°±2.0 for the base polyurethane substrate to 112.0°±2.1 for the BFSM modified material and parallel values with those of typical fluoropolymers, i.e. 116° for the advancing contact angle of Teflon®).

Figure 3:
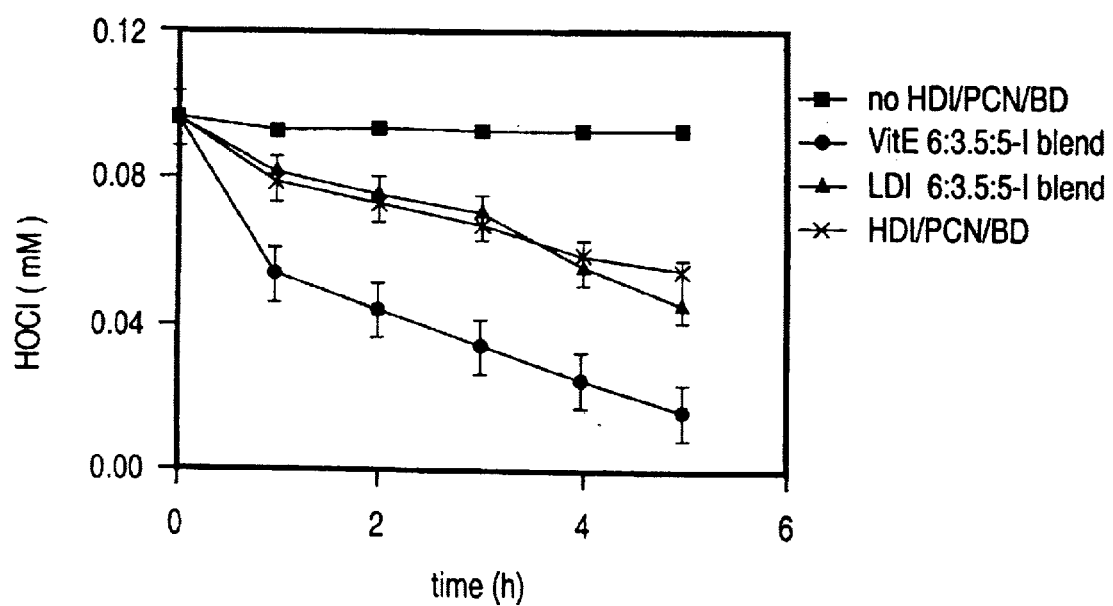
FIG. 3 demonstrates specific HOCl consumption by polyurethane base HDI/PCN/BD, base HDI/PCN/BD with non-bioactive surface modifier (LDI 6:3.5:5-I) and HDI/PCN/BD with 5 wt % of the BFSM, VITE 6:3.5:5-I (all three groups are compared to a blank control with no polymer)
Figure 4A:
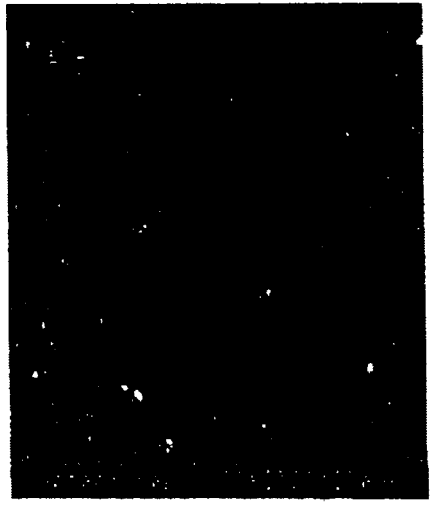
FIG. 4 is a SEM analysis of a polyurethane base HDI/PCN/BD and HDI/PCN/BD with 5 wt % of the BFSM, LDI/PCN/I/VITE.
Figure 4B:
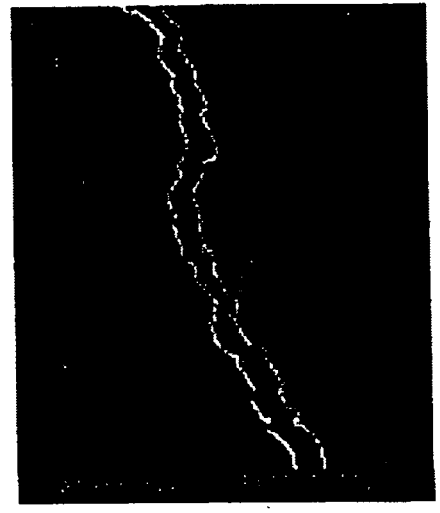
Figure 4C:
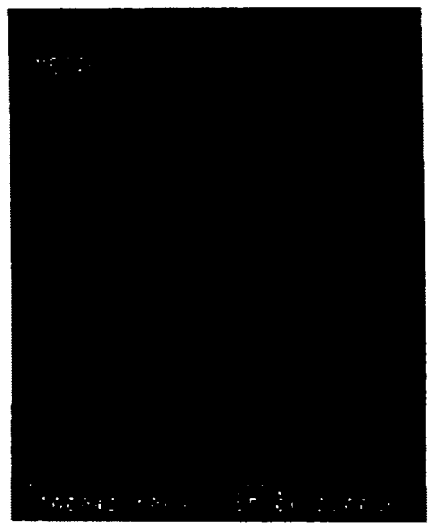
Figure 4D:
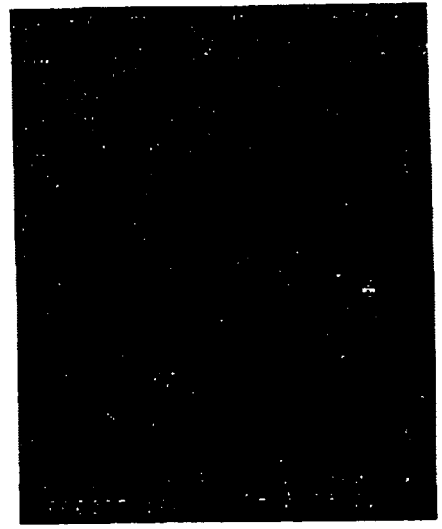

The presence of the vitamin-E at the surface cannot be confirmed by the XPS analytical system because it does not have the ability to resolve the chemical structure of vitamin-E relative to that of the base polyurethane. However, identification of the presence of Vitamin E can be provided by assessing its bioactivity. HOCl (hypochlorous acid) is an oxidative agent generated from activated white blood cells, associated with both neutrophils and monocytes. A measure of oxidant consumption in the presence of vitamin-E is a standard means of assessing the vitamin-E activity present. HDI/PCN/BD films with and without the BFSM were incubated with 10 mM hypochlorite, and the concentration of NaOCl was measured after 5 hours of exposure to the materials using a taurine-iodide colometric method. A calibration curve of NaOCl standards was prepared and analysed at 350 nm wavelength. It was shown that the vitamin-E-containing BFSM-HDI/PCN/BD surface consume 60% more NaOCl following 5 hours exposure to the oxidant than did the HDI/PCN/BD control—FIG. 3. This experiment confirmed the presence of the [Bio] component at the surface, adjacent to the [fluoro] segment. FIG. 3 demonstrates specific HOCl consumption by polyurethane base HDI/PCN/BD, base HDI/PCN/BD with non-bioactive surface modifier (LDI 6:3.5:5-I) and HDI/PCN/BD with 5 wt % of the BFSM, VITE 6:3.5:5-I (all three groups are compared to a blank control with no polymer), measured by spectrophotometric analysis of a taurine-iodide complex. The blank control consisted of 0.1 mM HOCl with no polymer. Error bars represent SE, n=3.

EXAMPLE 18

Upon the reaction of 5 wt % LDI/PDMS/I/NORF (Example 8) with MED10-6640 Silicone dispersion Pt catalyst, polydimethylsiloxane elastomer from Nusil Silicone Technology, and curing, it was observed that the additive migrated to the surface. Evidence of this is provided by X-ray photoelectron which showed the surface atomic fluorine content within the top 10 nm increased from background levels (<1 atomic weight %) to (>than 50 atomic weight %). This increase in fluorine content implies that more than 75% of the atoms on the surface are associated with the carbon/fluorine tails of the BFSM molecules. It also suggests that the fluorine and its immediately adjacent segments within the BFSM occupy a dominant component of the upper surface. The changes in surface chemistry are further with contact angle data, specifically advancing contact angle data. The advancing contact angle (which is a measure of the surface's hydrophobic components) show significant increases (from 115.0°±4.0 for the base polyurethane substrate to 125°±2.5 for the BFSM modified material) and exceeds values for those of typical fluoropolymers (i.e. 116° for the advancing contact angle of Teflon®). Note that silicone itself is a relatively hydrophobic material and the BFSM still it allowed to express is select surface chemistry in competition with siloxane groups.

This example in combination with Example 15 demonstrate the ability of the BFSM molecules to migrate to the surface of different polymeric substrates and dominate the surface function.

EXAMPLE 19

This example establishes the introduction of increased biocompatibility function at the surface of BFSM modified polymers. Specifically, the HDI/PCN/BD polymer substrate, when blended with 5 wt % LDI/PCN/I/VITE, exhibits a significant increased resistance to oxidation and chemical change following exposure to a biologically relevant oxidant, specifically HOCl. The hypochlorite ion is believed to be the direct oxidative component responsible in part for the oxidation of implant surfaces. Base polycarbonate urethane (HDI/PCN/BD) with and without LDI/PCN/I/VITE was incubated for 7 days, at 37° C. in 10 mM NaOCl. While both surfaces showed a reduction in molecular weight following the incubation period, 35% for the BFSM modified surface and 57% for the non-modified surface, the extent of chemical change to the polymer was significantly less with the surface modified material versus the non-modified material. This finding is further emphasized in the scanning electron microscopy (SEM) photographs of the two surfaces (FIG. 4). Cracking is clearly visible in the base polymer, and is minimal in the samples containing the BFSM.

A further analytical measurement of chemical change on the surface was demonstrated using attenuated total reflectance Fourier transform infra-red spectroscopy (ATR-FTIR) which analyses the top 1–5 microns of the surface chemistry. Polycarbonate polyurethanes contain both hydrogen and non-hydrogen bonded carbonyls. Studies have suggested that hydrogen bonded carbonyls are less susceptible to oxidation and hydrolysis. Conversely, non-hydrogen bonded carbonyls are susceptible to degradation. In this experiment, samples of HDI/PCN/BD were analysed by ATR-FTIR following incubation in NaOCl for 7 days at 37° C. The data show that the baseline ratio of H-bonded/non-bonded carbonate carbonyls is approximately 0.75 for the following three materials, namely, a) HDI/PCN/BD, b) HDI/PCN/BD with 5 wt % LDI/PCN/I/VITE (described in Example 1); and c) HDI/PCN/BD with 5 wt % LDI/PCN/I, which is a fluorinated surface modifying macromolecule without biofunctional capacity, i.e. no vitamin-E, but all other components being similar to the BFSM in Example 1), described in hereinbefore U.S. Pat. No. 6,127,507. Following incubation, the ratio for HDI/PCN/BD rose to 6.5 which indicates extensive disruption of the chemical structure in the polymer; and further confirming the degradation shown by FIG. 4. The HDI/PCN/BD with 5 wt % LDI/PCN/I/VITE sample showed no change in the H-bonded/non-bonded ratio while the sample containing the non-vitamin-E surface modifier showed an increase in H-bonded/non-bonded ratio of 2.5. This clearly indicates a chemical change in the polycarbonate segment of the base polymer. This latter data further illustrates the effectiveness of the LDI/PCN/I/VITE compound to provide a stable surface for the HDI/PCN/BD base, as well as demonstrated a significant added effect over prior art, specifically concerning surface modifying agents in the literature. FIG. 4 shows SEM analysis of HDI/PCN/BD and HDI/PCN/BD with 5 wt % LDI/PCN/I/VITE, following incubation in 10 mM NaOCl and phosphate buffer (pH=7.0) solutions for 7 days, 37° C. a.) HDI/PCN/BD in buffer, b.) HDI/PCN/BD in 10 mM NaOCl, c.) HDI/PCN/BD with BFSM in buffer, d.) HDI/PCN/BD with BFSM in buffer in 10 mM NaOCl.

EXAMPLE 20

Examples of biomedical articles that integrate the BFSM to the polymers using described methods 1, 2, 3 or 4 above include, for example, the following articles that are in whole or in part made of polyurethane components, namely, cardiac assist devices, tissue engineering polymeric scaffolds and related devices, cardiac replacement devices, cardiac septal patches, intra aortic balloons, percutaneous cardiac assist devices, extra-corporeal circuits, A-V fistual, dialysis components (tubing, filters, membranes, etc.), aphoresis units, membrane oxygenator, cardiac by-pass components (tubing, filters, etc.), pericardial sacs, contact lens, cochlear ear implants, sutures, sewing rings, cannulas, contraceptives, syringes, o-rings, bladders, penile implants, drug delivery systems, drainage tubes, pacemaker lead insulators, heart valves, blood bags, coatings for implantable wires, catheters, vascular stents, angioplasty balloons and devices, bandages, heart massage cups, tracheal tubes, mammary implant coatings, artificial ducts, craniofacial and maxillofacial reconstruction applications, ligaments, fallopian tubes, biosensors and bio-diagnostic substrates.

Non-biomedical articles fabricated by hereinbefore method 1) include, for example, extruded health care products, bio-reactor catalysis beds or affinity chromatography column packings, or a biosensor and bio-diagnostic substrates.

Non-medical application that are exemplified by method 2) include fibre membranes for water purification.

Non-medical applications of the type exemplified by method 3) and 4) include varnishes with anti-microbial function for aseptic surfaces.

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

What is claimed is:

1. A bioactive fluoroalkyl surface modifier for use in admixture with a compatible base polymer, said modifier having the general formula

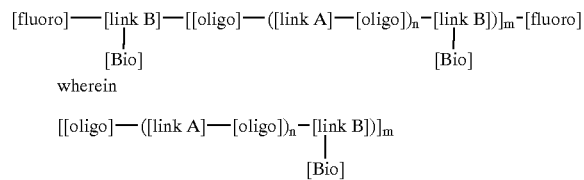

is a central portion comprising an oligomeric polymeric segment having a theoretical molecular weight of less than 15,000, and being compatible with said base polymer; wherein

[oligo] is a first oligomeric segment;

[link A] is a second coupling segment linking one [oligo] to another [oligo] within said central portion;

n is 0 to 20;

[fluoro] is a polyfluoro oligomeric group; and

[link B] is a first coupling segment linking said central portion to said [fluoro] through said first coupling segment; and coupled to a bioactive moiety [Bio] or precursor thereof; and m is 1 to 20.

2. A modifier as defined in claim 1 having the general formula

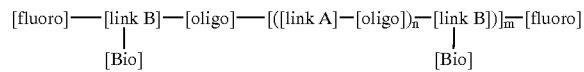

wherein n is 0–20; and m is 1–20;

provided that when n is 0, m is 1.

3. A modifier as defined in claim 1 wherein said oligomeric polymeric segment has an absolute molecular weight of less than 10,000.

4. A modifier as defined in claim 3 wherein said oligomeric polymeric segment has an absolute molecular weight of less than 5,000.

5. A modifier as defined in claim 1 wherein said [oligo] is selected from the group consisting of polyurethane, polyurea, polyamides, polyalkylene oxide, polycarbonate, polyester, polylactone, polysilicone, polyethersulfone, polyolefin, polyvinyl derivative, polypeptide and polysaccharide segments.

6. A modifier as defined in claim 1 wherein said [link A] and [link B] are selected from the group consisting of an oligoamide; oligourethane; oligourea; oligosulphonate; oligosulphonamide; oligoester; oligoacetal oligoimine segment, and combinations thereof.

7. A modifier as defined in claim 1 wherein said [fluoro] has a molecular weight selected from 100 to 1500.

8. A modifier as defined in claim 1 wherein said [fluoro] is selected from the group consisting of radicals of the general formula $CF_3(CF_2)_pCH_2CH_2$—wherein p is 2–20 and $CF_3(CF_2)_m(CH_2CH_2O)_q$- wherein q is 1–10 and m is 1–20.

9. A modifier as defined in claim 8 wherein said [fluoro] is $C_8F_{17}CH_2CH_2$-.

10. A modifier as defined in claim 1 wherein said bioactive moiety [Bio] is selected from the group consisting of an anti-inflammatory, anti-coagulant, anti-oxidant, antibiotic, cell receptor ligand, bioadhesive molecular, oligonucleic acid and phospholipid compound.

11. A modifier as defined in claim 10 wherein said bioactive material is selected from the group consisting of fluoroquinolone, Heparin, Hyaluronic acid, Vitamin E, peptide, hydrocortisone and L-α glycerophosphoryl choline.

12. A modifier as defined in claim 11 wherein said peptide is selected from GGRGD (SEQ ID NO: 5), YRGDG (SEQ ID NO: 3) and RGDSPASSKP (SEQ ID NO: 4).

13. A modifier as defined in claim 1 wherein n is 2 to 10.

14. A composition comprising a bioactive fluoroalkyl surface modifier as defined in claim 1 in admixture with said compatible base polymer.

15. A composition as defined in claim 14 wherein said base polymer is selected from the group consisting of polyurethanes, polysulfones, polycarbonates, polysaccharide, polyesters, polyethylene, polypropylene, polystyrene, poly(acrylonitrile-butadienestyrene), polybutadiene, polyisoprene, styrenebutadiene-styrene block copolymers, styrene-iso-prenestyrene block copolymers, poly-r-methylpentene, polyisobutylene, polymethyl-methacrylate, polyvinylacetate-polyacrylonitrile, polyvinyl chloride, polyethylene terephthalate, cellulose and its esters and derivatives, polyamides, polyester-polyethers, styrene-isoprenes, styrene butadienes, thermoplastic polyolefins, styrene-saturated olefins, polyester-polyester, ethylene-vinyl acetate ethylene-ethyl acrylate, ionomers, and thermoplastic polydienes.

16. A composition as defined in claim 15 wherein said base polymer is segmented polyurethane.

17. A composition as defined in claim 15 wherein said base polymer is selected from the group consisting of a polysilicone, a polyester, and a polysaccharide.

18. A composition as defined in claim 14 comprising 0.5 to 10 w/w % of said modifier.

19. A composition as defined in claim 18 comprising 1 to 5 w/w % of said modifier.

20. A composition as defined in claim 14 in the form of a shaped article.

21. A shaped article as defined in claim 20 in the form of an implantable medical device, self-supporting film, or fiber.

22. A modifier having the general formula

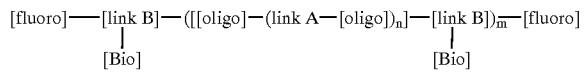

wherein $[[oligo]\text{-}(link\ A\text{-}[oligo])_n]$ is a central portion comprising an oligomeric polymeric segment having a theoretical molecular weight of less than 15,000, and being compatible with said base polymer;

[oligo] is a first oligomeric segment;

[link A] is a second coupling segment linking one [oligo] to another [oligo] within said central portion;

n is 0 to 20;

[fluoro] is a polyfluoro oligomeric group; and

[link B] is a first coupling segment linking said central portion to said [fluoro] through said first coupling segment; and coupled to a bioactive moiety [Bio] or precursor thereof; and m is 1 to 20.

* * * * *

SEQUENCE LISTING

```
<160> NUMBER OF SEQ ID NOS: 6

<210> SEQ ID NO 1
<211> LENGTH: 47
<212> TYPE: DNA
<213> ORGANISM: Artificial sequence
<220> FEATURE:
<223> OTHER INFORMATION: GHG probe

<400> SEQUENCE: 1
atactgagat gggtgccgtt ctatgactct acccacggca agttcaa          47

<210> SEQ ID NO 2
<211> LENGTH: 5
<212> TYPE: PRT
<213> ORGANISM: Artificial sequence
<220> FEATURE:
<223> OTHER INFORMATION: synthetic polypeptide that promotes cell
      activation and spreading

<400> SEQUENCE: 2

Pro His Ser Arg Asn
1               5

<210> SEQ ID NO 3
<211> LENGTH: 5
<212> TYPE: PRT
<213> ORGANISM: Artificial sequence
<220> FEATURE:
<223> OTHER INFORMATION: synthetic polypeptide that promotes cell
      activation and spreading

<400> SEQUENCE: 3

Tyr Arg Gly Asp Gly
1               5

<210> SEQ ID NO 4
<211> LENGTH: 10
<212> TYPE: PRT
<213> ORGANISM: Artificial sequence
<220> FEATURE:
<223> OTHER INFORMATION: synthetic polypeptide that promotes cell
      activation and spreading

<400> SEQUENCE: 4

Arg Gly Asp Ser Pro Ala Ser Ser Lys Pro
1               5                   10
```

```
<210> SEQ ID NO 5
<211> LENGTH: 5
<212> TYPE: PRT
<213> ORGANISM: Artificial sequence
<220> FEATURE:
<223> OTHER INFORMATION: synthetic polypeptide with binding affinity
      to cell receptors and integrins

<400> SEQUENCE: 5

Gly Gly Arg Gly Asp
1               5

<210> SEQ ID NO 6
<211> LENGTH: 26
<212> TYPE: DNA
<213> ORGANISM: Artificial sequence
<220> FEATURE:
<223> OTHER INFORMATION: GHG probe

<400> SEQUENCE: 6
tatgactcta cccacggcaa gttcaa                                          26
```